United States Patent
George et al.

(10) Patent No.: US 6,866,637 B2
(45) Date of Patent: Mar. 15, 2005

(54) APPARATUS AND METHOD FOR THE ESTIMATION OF FLOW -INDEPENDENT PARAMETERS WHICH CHARACTERIZE THE RELEVANT FEATURES OF NITRIC OXIDE PRODUCTION AND EXCHANGE IN THE HUMAN LUNGS

(75) Inventors: Steven C. George, Irvine, CA (US); Nikolaos Tsoukias, Baltimore, MD (US)

(73) Assignee: The Regents of the University of California, Oakland, CA (US)

( * ) Notice: Subject to any disclaimer, the term of this patent is extended or adjusted under 35 U.S.C. 154(b) by 290 days.

(21) Appl. No.: 10/257,789

(22) PCT Filed: Apr. 26, 2001

(86) PCT No.: PCT/US01/13851

§ 371 (c)(1),
(2), (4) Date: Oct. 17, 2002

(87) PCT Pub. No.: WO01/82782

PCT Pub. Date: Nov. 8, 2001

(65) Prior Publication Data

US 2003/0208131 A1 Nov. 6, 2003

Related U.S. Application Data

(60) Provisional application No. 60/200,682, filed on Apr. 29, 2000.

(51) Int. Cl.[7] .................................................. A61B 5/00
(52) U.S. Cl. .................... 600/532; 73/23.3; 600/538
(58) Field of Search ............................. 600/532; 7/538; 73/23.3; 422/84

(56) References Cited

U.S. PATENT DOCUMENTS

| | | | | |
|---|---|---|---|---|
| 5,447,165 A | * | 9/1995 | Gustafsson | 600/532 |
| 5,922,610 A | * | 7/1999 | Alving et al. | 436/116 |
| 6,010,459 A | * | 1/2000 | Silkoff et al. | 600/532 |
| 6,033,368 A | * | 3/2000 | Gaston et al. | 600/532 |
| 6,038,913 A | * | 3/2000 | Gustafsson et al. | 73/23.3 |
| 6,099,480 A | * | 8/2000 | Gustafsson | 600/532 |
| 6,612,306 B1 | * | 9/2003 | Mault | 128/204.22 |

* cited by examiner

Primary Examiner—Robert L. Nasser
(74) Attorney, Agent, or Firm—Daniel L. Dawes; Myers Dawes Andras & Sherman LLP

(57) ABSTRACT

The invention provides an estimation of key flow-independent parameters characteristic of NO exchange in the lungs, namely: 1) the steady state alveolar concentration, $C_{alv,ss}$; 2) the maximum flux of NO from the airways, $J_{NO,max}$; and 3) the diffusing capacity of NO in the airways, $D_{NO,air}$. The parameters were estimated from a single exhalation maneuver comprised of a pre-expiratory breathhold, followed by an exhalation in which the flow rate progressively decreased. The mean values for $J_{NO,max}$, $D_{NO,air}$, and $C_{alv,ss}$ do not depend on breathhold time for breathhold times greater than approximately 10 seconds. A priori estimates of the parameter confidence intervals demonstrates that a breathhold no longer than 20 seconds may be adequate, and that $J_{NO,max}$ be can estimated with the smallest uncertainty, and $D_{NO,air}$ the largest.

34 Claims, 8 Drawing Sheets

APPARATUS AND METHOD FOR THE ESTIMATION OF FLOW-INDEPENDENT PARAMETERS WHICH CHARACTERIZE THE RELEVANT FEATURES OF NITRIC OXIDE PRODUCTION AND EXCHANGE IN THE HUMAN LUNGS

RELATED APPLICATIONS

The present application is related to and is a continuation in part of U.S. Provisional application Ser. No. 60/200,682, filed Apr. 29, 2000, which is incorporated herein by reference.

BACKGROUND OF THE INVENTION

1. Field of the Invention

The invention relates to a method and apparatus for determining physiological parameters indicative of lung condition, which parameters are independent of air flow rates based on nitrogen monoxide content in exhalation, which content is dependent on air flow rates.

2. Description of the Prior Art

The concentration of nitric oxide (NO) that appears in the exhaled breath depends strongly on several factors including the presence of inflammation. The fact that inflammatory diseases, such as bronchial asthma, elevate exhaled NO has generated great interest in using exhaled NO as a non-invasive index of pulmonary inflammation. Unfortunately, many early reports collected NO levels under different experimental conditions, and the absolute concentrations, as well as the conclusions, were not consistent. Subsequent work demonstrated that the exhaled NO level also depends on many additional factors including the exhalation flow rate, and the position of the soft palate (which affects nasal cavity contribution). These findings generated formal recommendations by both the American Thoracic Society (ATS) and the European Respiratory Society (ERS) on the conditions under which exhaled NO should be collected. Both reports recommend a constant exhalation flow rate during the maneuver (ERS recommends 250 ml/s, the ATS recommends 50 ml/s).

Recently, several groups have demonstrated that exhaled NO arises from both the alveolar and airway regions of the lungs; this conclusion is supported by the presence of nitric oxide synthase (NOS) in cells present in both regions. The flow rate dependence is due to the source of NO in the airways, and this finding prompted the recommendation of a single constant flow rate in all experimental protocols. However, this recommendation presents a critical limitation in the interpretation of the exhaled NO. Namely, the constant flow rate maneuver cannot provide information regarding the origin of the endogenous NO production (i.e. the relative contribution from the airways and the alveoli). As a result, a single exhalation with a constant exhalation flow rate is inherently non-specific, since two subjects can potentially have the same exhaled NO concentration, yet different relative contributions from the airways and alveoli. For example, two subjects with different inflammatory diseases (i.e., asthma and allergic alveolitis) could have identical exhaled NO levels at a constant exhalation flow. The exhaled NO from the patient with asthma would largely arise from the airways, while the exhaled NO from the patient with allergic alveolitis (alveolar inflammation) would largely arise from the alveolar region. However, by using only the exhaled concentration at a single expiratory flow as an index, the diseases could not be distinguished.

To avoid this problem, the prior art has used a technique that utilized multiple single exhalation maneuvers at different constant exhalation flow rates as a means of separately determining airway and alveolar contributions. The airway contribution was characterized by the flux from the airway wall (moles NO/s or ml NO/s) and the alveolar contribution by the steady state alveolar concentration (ppb). Recently, two research groups reported an alternative technique in which the flux from the airway compartment 10 was characterized by two terms—the airway diffusing capacity and either the airway wall concentration or the maximum rate of production of NO by the airways which enters the airstream (maximum flux of NO from the airways). This was achieved by utilizing very low constant expiratory flow rate maneuvers. All of the previous techniques require multiple single exhalations, and the accuracy (or confidence level) of the estimated parameters is positively correlated with the number of single exhalations utilized. Multiple breathing maneuvers are cumbersome and time consuming. Furthermore, constant flow rate maneuvers can be difficult to perform, especially at very low flows and by young subjects.

What is needed is a technique to characterize NO exchange parameters without requiring a constant flow rate.

BRIEF SUMMARY OF THE INVENTION

The method of the invention involves an appropriate analysis of an individual (i.e., not multiple) single exhalation maneuver with a variable flow rate. The technique allows: 1) estimation of flow-independent parameters characteristic of NO exchange dynamics from a single maneuver, and 2) prediction of the plateau NO concentration at a constant exhalation flow rate. The new method of analysis is more versatile, since it provides a means to analyze exhaled NO data when flow rate is not necessarily constant.

Furthermore, by inducing specific changes in flow rate during a single exhalation, the technique renders a single exhalation maneuver sufficient to acquire all the necessary information. The theory underlying the technique and a test of this technique in two normal subjects (one experienced and one naïve to breathing maneuvers), is described below. A characterization of the intrinsic intra-maneuver and intra-subject variability; in particular, the effect of breathhold time on the variability of the estimated parameters is provided.

More specifically, the invention is defined as a method for determining flow independent parameters characteristic of NO exchange and lung function in a subject during one exhalation during which the flow rate of exhalation varies in time. The method comprises the steps of exhaling into a mouthpiece in which the resistance to airflow is variable, measuring the exhaled nitrogen monoxide concentration, $C_{exh}$, from the subject as a function of time by sampling from the exhaled breath, and simultaneously measuring the volumetric exhalation flow rate. $\dot{V}_E$. as a function of time. The volumetric exhalation flow rate, $\dot{V}_E$, is backwards integrated over time to convert exhalation time to residence time of each exhaled bolus of gas in the airway compartment of the subject. The flow independent parameters are derived or selected to fit the measured nitrogen monoxide concentration as a function of time given residence time obtained by backwards integration.

The method further comprises the step of estimating, $V_{air}$, which is the volume of the airway compartment of the subject, and measuring $V_{ds}$ which is the dead space volume or volume expired prior to observing a NO signal. The exhalation flow rate, $\dot{V}_E$, is backwards integrated over time to convert exhalation time to residence time of each exhaled bolus of gas in the airway compartment in the subject. The backwards integration is performed in a computer according to a Case I or Case II integration where:

Case I (Phase I and II of exhalation): $\int_{t-\tau_{res}(t)}^{t+t_{ds}} \dot{V}_E(t') dt' = 0$ Case II (Phase III of exhalation): $\int_{t-\tau_{res}(t)}^{t+t_{ds}} \dot{V}_E(t') dt' = V_{air} + V_{ds}$ where t is time, $t_{ds}$ is convective transport delay time in the dead space volume, $T_{res}$ is residence time of each differential gas bolus in the airway compartment.

The step of selecting the flow independent parameters to fit the measured nitrogen monoxide concentration comprises estimating three flow-independent parameters $C_{alv,ss}$, $D_{NO,air}$, $J_{NO,max}$ from $C_{exh}$ as a function of $T_{res}(t)$, where $C_{alv,ss}$ is the steady state alveolar concentration of nitrogen monoxide. $D_{NO,air}$ is the diffusing capacity of nitrogen monoxide in the airway compartment. $J_{NO,max}$ is the maximum total molar flux of nitrogen monoxide from the airway wall. Although not an independent parameter, the ratio of $J_{NO,max}$ and $D_{NO,air}$ is equal to the mean tissue concentration of NO in the airway compartment, $C_{tiss,air}$, and may also prove useful as an index of lung function. $C_{exh}$ is the exhaled concentration of nitrogen monoxide, and $T_{res}(t)$ is the residence time of each differential gas bolus in the airway compartment as a function of time, t.

The step of estimating the three flow-independent parameters $C_{alv,ss}$, $D_{NO,air}$, $J_{NO,max}$ from $C_{exh}$ as a function of $T_{res}(t)$ comprises the step of performing the estimation by relating the three flow-independent parameters $C_{alv,ss}$, $D_{NO,air}$, $J_{NO,max}$ and $C_{exh}$ to the experimentally measured exhaled concentration and flow rate in a computer in the relationship given by:

$$C_{exh}(t+t_{ds}) = \left(C_{in}(t-\tau_{res}) - \frac{J_{NO,max}}{D_{NO,air}}\right) e^{-\frac{D_{NO,air}}{V_{air}}\tau_{res}(t)} + \frac{J_{NO,max}}{D_{NO,air}}$$

where $C_{in}$ is the inlet concentration of nitrogen monoxide to the airway compartment.

The step of measuring nitrogen monoxide concentration as a function of time comprises the step of performing the measurement of the exhaled bolus of gas with multiple residence times in which one must be at least ten seconds. In the preferred embodiment this is accomplished by performing a pre-expiratory breathhold of 10, 20, 30 or 45 seconds. Other breathhold durations could be chosen according to the spirit and teachings of the invention.

In one embodiment the step of exhaling into the nitrogen monoxide concentration analyzer comprises the step of providing an approximately exponentially decreasing flow of exhalation in time, which generates a uniform distribution of residence times. Although this is an optimal condition, it is not a requirement. If a maneuver is performed in which the flow rate of exhalation does not decreases exponentially this will be reflected in a greater uncertainty in the estimate of the parameter. In addition, the flow rate need not be restricted to decreasing during exhalation, but may increase. The key is a variable flow rate in which the flow rate history of each differential bolus air is known by measuring the exhalation flow simultaneously with nitrogen monoxide content.

In addition, there must be a minimal acceleration of the exhaled bolus of gas in the airway compartment. In other words the step of exhaling into the mouthpiece with a variable resistance to flow comprises the step of establishing the residence time for each differential bolus of gas as an approximate linear function of time. t. More specifically, the step of establishing the residence time for each differential bolus of gas as a linear function of time, t, comprises exhaling such that $$\dot{V}_E = 1/(\dot{V}_{E0}^{-1} + ct)$$

is approximated, where $\dot{V}_E$ is the time dependent rate of exhalation, $\dot{V}_{E0}$ is the initial flow rate of exhalation and c is a linear multiplier.

The step of selecting the flow independent parameters to fit the measured nitrogen monoxide concentration comprises optimizing the flow independent parameters by performing a nonlinear least square minimization of $C_{exh}$. More specifically, optimizing the flow independent parameters by performing a nonlinear least square minimization of $C_{exh}$ comprises the step of minimizing a sum of two terms: 1) the squared residual in the average concentrations in Phase I and II weighted by the number of data points. and 2) the sum of the squared residual of $C_{exh}$ in Phase III of the exhalation profile according to the following relationship:

$$R_{LS} = n_{I,II} \cdot \left(\left(\sum_{i=1}^{n_{I,II}} C^*_{exh,i} \cdot \Delta V_{I,II}\right) / V_{I,II} - \left(\sum_{i=1}^{n_{I,II}} C_{exh,i} \cdot \Delta V_{I,II}\right) / V_{I,II}\right)^2 + \sum_{i=1}^{n_{I,II}} (C^*_{exh,i} - C_{exh,i})^2 \tag{7}$$

where $n_{I,II}$ and $V_{I,II}$ are the number of data points and volume in Phase I and II respectively. $n_{III}$ and $V_{III}$ are the number of data points and volume in Phase III. $C^*_{exh}$ is the model-predicted concentration. and $\Delta V_{I,II}$ is the change in volume between consecutive data points. ($\dot{V}_E$*dt). in Phase I and II respectively.

The step of exhaling into a flow rate and nitrogen monoxide concentration analyzer includes within its scope tidal breathing by the subject.

The invention is also defined as an apparatus for performing the above methodology.

While the method has been described for the sake of grammatical fluidity as steps, it is to be expressly understood that the claims are not to be construed as necessarily limited in any way by the construction of "means" or "steps" limitations under 35 USC 112, but to be accorded the full scope of the meaning and equivalents of the definition provided by the claims whether by the judicial doctrine of equivalents or by statutory equivalents under 35 USC 112. The invention can be better visualized by turning now to the following drawings wherein like elements are referenced by like numerals.

Figure 1:
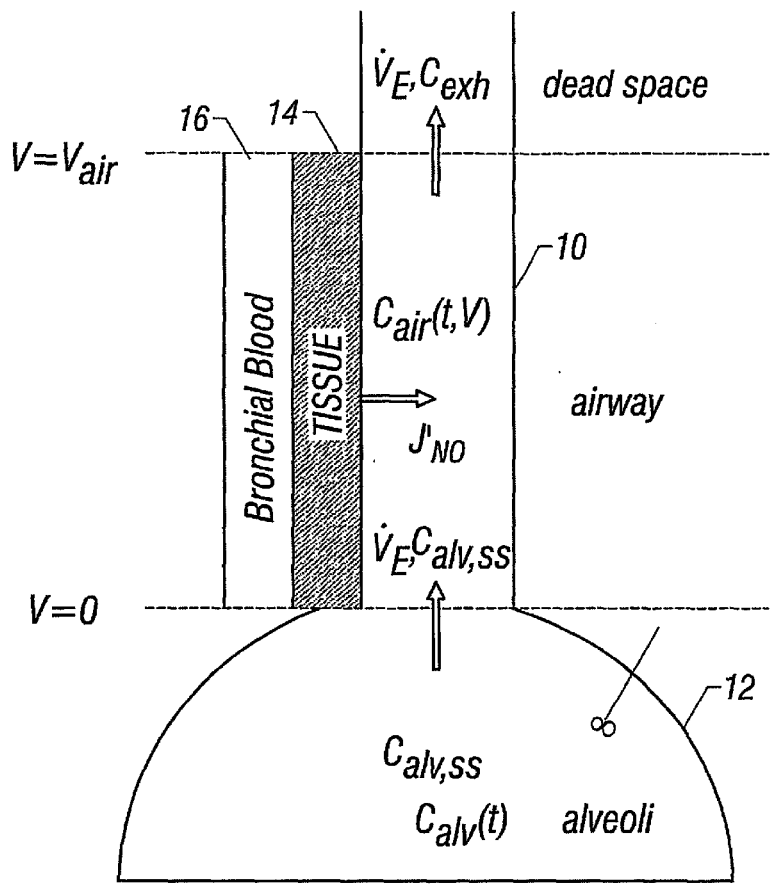
FIG. 1 is a diagram of a two-compartment model used to describe NO exchange dynamics. The alveolar compartment 12 has been simplified to represent only the steady state concentration during exhalation.

The invention and its various embodiments can now be better understood by turning to the following detailed description of the preferred embodiments which are presented as illustrated examples of the invention defined in the claims. It is expressly understood that the invention as defined by the claims may be broader than the illustrated embodiments described below.

DETAILED DESCRIPTION OF THE PREFERRED EMBODIMENTS

One embodiment of the invention is based on the use of a two-compartment model. A simple two-compartment mathematical model has been previously developed to describe the exchange dynamics of NO in the human lungs. We will utilize the governing equations of this model in our parameter estimation algorithm, and will review only the salient features here. The model is summarized pictorially in FIG. 1, and is comprised of a rigid tubular compartment 10 representing the airways (trachea-airway generation) and a well-mixed expansile compartment 12 representing the alveoli (airway generation and beyond). A tissue layer 14 representing the bronchial mucosa surrounds the airway 10. Exterior to the tissue 14 is a layer of blood 16 representing the bronchial circulation, and serves as an infinite sink for NO (i.e., zero concentration of NO).

The axial gas phase transport is characterized by bulk convection (advection). The tissue phase produces NO uniformly, and at a constant rate, and consumes NO in a first order fashion. The outer boundary of the tissue 14 is assumed to be blood. Since the reaction of NO with hemoglobin within the red cell is very rapid, and there are abundant protein-thiols (e.g., albumin) in plasma, the concentration of free NO in the blood is assumed to be zero. Transport between the tissue and gas phase is described with Fick's 1st Law of Diffusion. The concentration profile in the tissue has been shown to rapidly (<0.6 seconds) reach a steady state; thus, the mass balance in the airway compartment 10 retains an analytical solution. The second compartment 12 represents the alveolar regions of the lungs, and is thus expansile and 10 considered to have a uniform concentration spatially. The model of FIG. 1 is meant to simulate the oral exhalation profile, and thus assumes that there is no nasal contribution to exhaled NO.

Before proceeding with the discussion of the model of FIG. 1 note should be made of the following glossary of terms which are used in this disclosure.

| | |
|---|---|
| $C_{air}(t,V)$: | concentration (ppb) of NO in the airway compartment 10 |
| $C_{alv,ss}$: | steady-state alveolar concentration of NO (ppb) |
| $C_{exh}$: | exhaled concentration (ppb) |
| $C^*_{exh}$: | model-predicted exhaled concentration (ppb) |
| $C_I$: | inspired concentration (ppb) |
| $\overline{C}_{tiss,air}$: | mean (over radial position) concentration of NO within the tissue phase (ppb) |
| $D_{NO,air}$: | diffusing capacity (ml · s$^{-1}$ · ppb$^{-1}$) of NO in the airways |
| F: | F-statistic test |
| $\Delta \bar{I}_{1-\alpha,i}^m \alpha$. | intra-maneuver 100(1-α) % confidence interval |
| $\Delta \bar{I}_{1-\alpha,i}^s \alpha$ | intra-subject 100(1-α) % confidence interval |
| $J'_{NO}$ ($C_{air}$): | volumetric flux per unit airway volume (ml · s$^{-1}$ · ml$^{-1}$ = ppb · s$^{-1}$ × 10$^{-9}$) of NO |
| $J_{NO,max}$: | maximum total molar flux (ml/s) of NO from the airway wall |
| n: | number of data points |
| P: | covariance matrix |
| $t_{ds}$: | convective transport delay time in the dead space volume |
| $T_{res}$: | residence time of each differential gas bolus in the airway compartment 10 |
| $S^{sr}$: | semi-relative sensitivity index |
| V: | axial (or longitudinal) position from the distal region of the airway to the mouth |
| $V_{air}$: | volume of the airway compartment 10 (ml) |
| $V_{ds}$: | dead space volume (volume expired prior to observing NO signal) (ml) |
| $\dot{V}_E$: | volumetric flow rate of air during expiration |
| $\dot{V}_I$: | volumetric flow rate of air during inspiration |
| $Y_{1-s}$: | 100(1-□) % confidence region for the the vector of inputs |

We, as well as other researchers, have previously demonstrated that $C_{alv}$ reaches a steady state concentration in <10 seconds following inspiration. Thus, in the development of our current technique, we have simplified the alveolar compartment 12, and will characterize the alveolar region by the steady state alveolar concentration, $C_{alv,ss}$. This simplification is justified for inspiration of NO-free air, and for exhalation following at least a 10 second breathhold. It is important to note that if the general principles (i.e. $C_{alv,ss}$ as a function of the flow rate, $\dot{V}_E$,) were applied to tidal breathing, $C_{alv,ss}$ would not be appropriate, and a time-dependent alveolar concentration would need to be utilized.

A mass balance in the airway compartment 10 produces the following differential equation:

$$\frac{\partial C_{air}}{\partial t} = -\dot{V}(t)\frac{\partial C_{air}}{\partial V} + J'_{NO}(C_{air}) \quad (1)$$

where $C_{air}(t,V)$ is the concentration (ppb) of NO in the airway compartment 10; $J'_{NO}$ ($C_{air}$) is the volumetric flux per unit airway volume (ml·s$^{-1}$·ml$^{-1}$=ppb·s$^{-1}$×10$^{-9}$) of NO between the tissue and gas phases in the airway compartment 10 and depends on $C_{air}$; $\dot{V}(t)$ is volumetric flow rate of air (negative during inspiration $\dot{V}_I$, and positive during expiration $\dot{V}_E$); and V is the axial (or longitudinal) position from the distal region of the airway to the mouth of the patient in units of cumulative volume.

Flux of NO from Airway Wall.

A prior art description of the exchange dynamics in the airway tissue layer, that incorporates endogenous production, reaction and diffusion, predicts $J'_{NO}$ to be a linear function of the bulk gas concentration. In agreement with the prior art, we assume a uniform distribution for $J'_{NO}$ along the airway tree (i.e. the same linear dependence between $J'_{NO}$ and $C_{air}$ holds throughout the airways 10). Then the following linear relationship between $J'_{NO}$ and $C_{air}$ holds:

$$J'_{NO} = \left(\frac{J_{NO,max}}{V_{air}}\right) - \left(\frac{D_{NO,air}}{V_{air}}\right) * C_{air} \quad (2)$$

where $V_{air}$ is the volume (ml) of the airway compartment 10, and $J_{NO,max}$ represents the maximum total volumetric flux (ml/s) of NO from the airway wall (i.e., the total flux when $C_{air}$ is zero). $D_{NO,air}$ is the diffusing capacity (ml·s$^{-1}$·ppb) of NO in the airways. Thus, we will characterize $J'_{NO}$ with two parameters: $J_{NO,max}$ and $D_{NO,air}$.

Model Solution.

Assuming a spatially uniform distribution of $J'_{NO}$, the solution for the exhaled concentration, $C_{exh}$, which follows from Eq. 1 and 2 above, has the following form:

$$C_{exh}(t + t_{ds}) = C_{air}(t, V = V_{air}) = \quad (3)$$

$$\left(C_{in}(t - \tau_{res}) - \frac{J_{NO,max}}{D_{NO,air}}\right)e^{-\frac{D_{NO,air}}{V_{air}}\tau_{res}(t)} + \frac{J_{NO,max}}{D_{NO,air}}$$

where $C_{in}$ is the inlet concentration to the airway compartment 10, $T_{res}$ is the residence time of each differential gas bolus in the airway compartment 10, $V_{ds}$ is the dead space volume (volume expired prior to non-zero NO concentration, ~75 ml), and $t_{ds}$ is the convective transport delay time in $V_{ds}$. We can distinguish two different cases:

$$\text{Case I (Phase I and II of exhalation): } \int_{t-\tau_{res}(t)}^{t+t_{ds}} \dot{V}_E(t')dt' = 0 \quad (4)$$

$$\text{Case II (Phase III of exhalation): } \int_{t-\tau_{res}(t)}^{t+t_{ds}} \dot{V}_E(t')dt' = V_{air} + V_{ds} \quad (5)$$

Case I represents the emptying of the gas in Phase I and II of the exhalation profile (see below). Phase I is defined as that portion of the exhalation profile which represents air which has only resided in the airways. Phase II is defined as that portion of the exhalation profile which represents gas from both the airway and alveolar compartments, and Phase III is defined as that part of the exhalation profile which represents gas which originates solely from the alveolar region but is then convected through the airway compartment. During inspiration, $C_{in}$ is simply the inspired concentration $C_I$ ($C_I$=0 by ATS guidelines) and $T_{res}(t)$ is calculated from Eq. 4. In other words, the net volume transpired by each bolus is zero, and is given by the integral of the flow rate over the time period of interest. The flow signal during this time period would include inspiration (negative flow rate), breathhold (zero flow rate), and expiration (positive flow rate).

Case II represents the emptying of the gas in Phase III of the exhalation profile, or the alveolar plateau. Phase II is not described by the model as axial diffusion is neglected to preserve an analytical solution; the compensation for this simplification is described in Parameter Estimation. During Phase III, the expired air originates primarily from the alveolar compartment 12. Thus, $C_{in}$ is equivalent to $C_{alv,ss}$, and $T_{res}(t)$ is calculated from Eq. 5. In this case, the flow signal is provided entirely by the expiratory flow rate.

Figure 2:
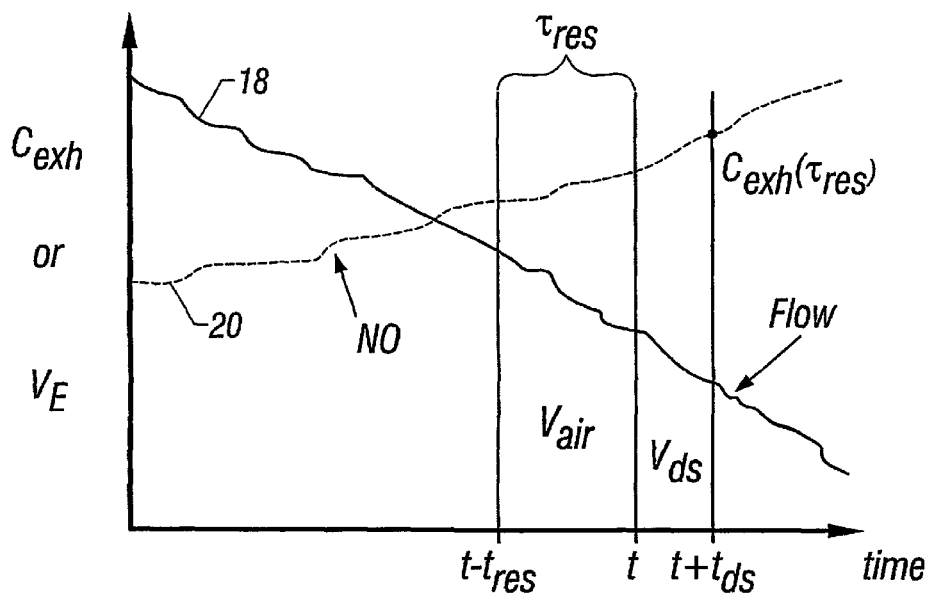
FIG. 2 is a graph demonstrating the "backward" integration of the flow signal to convert exhalation time to residence time of each exhaled bolus of gas.
Figure 4:
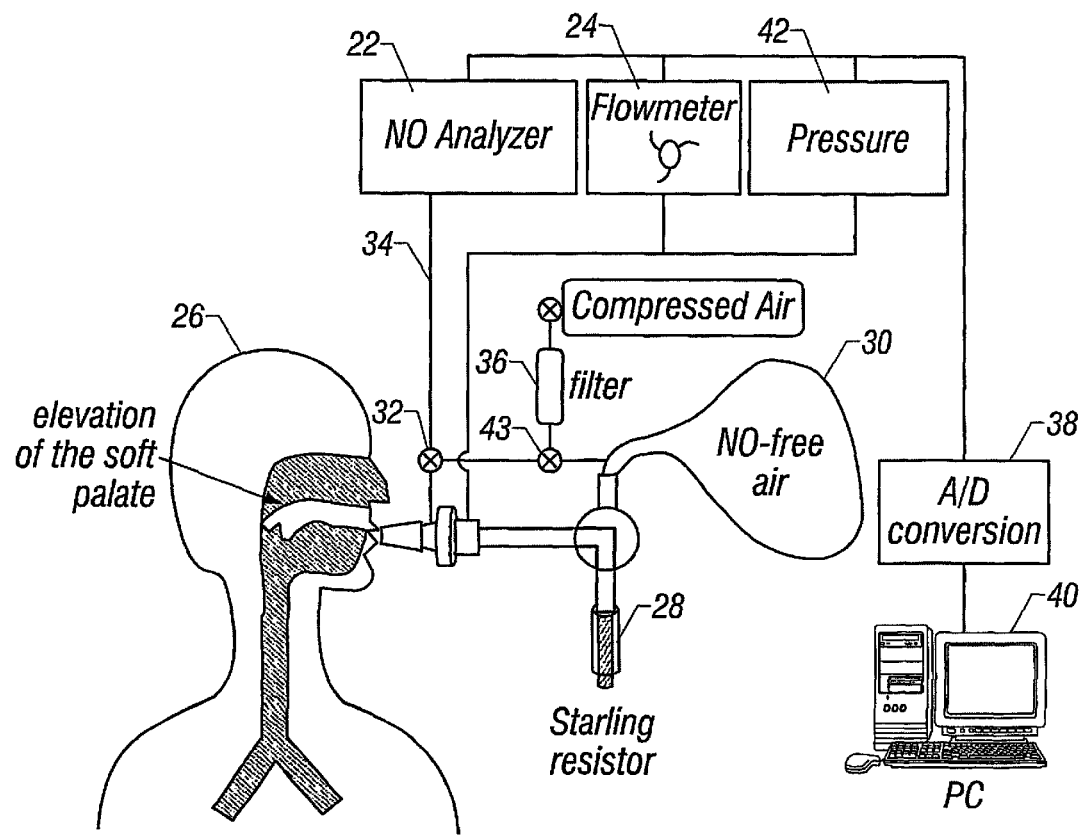
FIG. 4 is a block diagram of the experimental setup used to collect the exhalation profiles.

FIG. 2 is a graph which depicts the method used for analyzing the experimental data (Eq. 3–5) and demonstrating the "backward" integration of the flow signal to convert exhalation time to residence time of each exhaled bolus of gas. The concentration of a gas bolus is determined at time $t+t_{ds}$. By using the flow rate history of the bolus, one can integrate the flow rate signal backward until the volume of the deadspace and the airway volume has been traversed. In doing so, one can determine the residence time in the airway compartment 10. The flow shown by curve 18 and NO signal shown by curve 20 were first synchronized to account for the delay of the NO analyzer 22 relative to the flow meter 24 shown in FIG. 4. FIG. 4 is a block diagram of the experimental setup used to collect the exhalation profiles. The flow, pressure, and NO analog signals are captured by the analytical instruments and converted to a digital signal. A series of valves allows NO-free air to be stored in a mylar bag 30 for inspiration. During the breathhold, the NO analyzer 22 samples from the NO-free air reservoir 30, and the subject maintains a positive pressure of >5 cmH$_2$O by attempting to exhale against a closed valve 43. As exhalation begins, the NO analyzer 22 then samples from the exhalate and the flow rate is manipulated by a variable Starling resistor 28 while the expiratory effort of the subject remains constant. Then, for a bolus of gas that reaches the sampling port of the analyzer 22 at time $t+t_{ds}$, $t_{ds}$ and $T_{res}$ can be estimated using backward integration of the expiratory flow signal if $V_{ds}$ and $V_{air}$ are known. $V_{ds}$ is approximated from the volume the subject needs to expire prior to observing a change in $C_{exh}$ (after the signals have been synchronized). A first approximation of $V_{air}$ will be the physiological dead space in ml, as approximated by the weight (assuming normal body fat) of the subject in pounds plus the age of the subject in years. During the backward integration, each exhaled bolus is treated according to Case I or II depending on whether the condition of Eq. 4 and 5 is satisfied. Eq. 3 can be used to simulate the experimental profiles.

Eqs. 3–5 allow analysis of a single exhalation with a variable flow rate. Together, the equations simply state that in the absence of interaction between neighboring differential boluses of gas (i.e. no axial diffusion), and for a uniformly distributed $J'_{NO}$, $C_{exh}(t)$ will depend on only five unknown parameters: $C_{alv,ss}$, $D_{NO,air}$, $J_{NO,max}$, $V_{air}$, and $T_{res}(t)$. If one has a previous estimate of $V_{air}$, one can then determine $T_{res}(t)$ from Eq. 4 and 5, and the problem is reduced to estimating three flow-independent parameters ($C_{alv,ss}$, $D_{NO,air}$, $J_{NO,max}$) from $C_{exh}$ as a function of $T_{res}(t)$.

Sensitivity Analysis

We define the semi-relative sensitivity of $C_{exh}$ with respect to the unknown parameters in the following fashion:

$$S_i^{sr} = Y_i \frac{\partial C_{exh}}{\partial Y_i} \quad (6)$$

where Y is one of the unknown parameters, and the subscript "i" represents the specific parameter. The derivatives are estimated at the nominal values of each parameter. $S^{sr}$ represents the absolute change of $C_{exh}$ per fractional change of the corresponding parameter, and is useful for: 1) providing a useful relative index of comparison between the unknown parameters and their impact on $C_{exh}$, and 2) determining the confidence region of the estimated parameters. The partial derivatives can be calculated analytically by differentiation of Eq. 2 with respect to the corresponding variable. A necessary condition for an accurate estimation of the parameters of interest is that the model's output should be sensitive enough relative to the intrinsic error of the experimental measurement.

Figure 3:
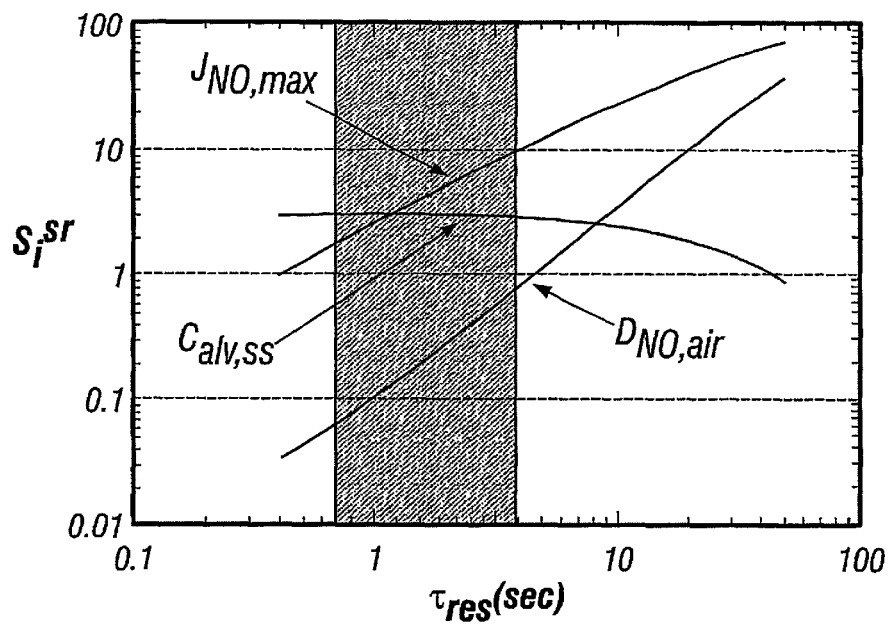
FIG. 3 is a graph illustrating the semi-relative sensitivity of the exhaled concentration, $C_{exh}$, to the three input parameters.

In FIG. 3 we plot $S^{sr}$ as a function of $T_{res}$. FIG. 3 illustrates the semi-relative sensitivity of the exhaled concentration, $C_{exh}$, to the three input parameters. The shaded region represents the range of airway compartment residence times achieved during a decreasing flow rate maneuver that spans an exhalation flow rate of 300 to 50 ml/s for an airway compartment volume of 200 ml. It is clear that $C_{exh}$ is quite sensitive to $J_{NO,max}$ and $C_{alv,ss}$; however, $S_{D_{NO,air}}^{sr}$ is high only for high $T_{res}$. The analysis suggests that residence times >10 seconds are required to achieve a similar sensitivity index (and thus confidence in the estimate) as that obtained for $J_{NO,max}$ and $C_{alv,ss}$ at a residence of time of ~1 second. This is consistent with the need to utilize very small flow rates (<10 ml/s) in prior art attempts to estimate $D_{NO,air}$. In practice, we found that it is difficult to perform such a maneuver; especially by young subjects, and accurately record such low flow rates. Alternatively, we utilize a pre-expiratory breathhold to produce large enough residence times to accurately estimate $D_{NO,air}$.

Experimental Protocol.

A series of single exhalation maneuvers were performed on two subjects, one experienced and one naive to performing breathing maneuvers, to determine the feasibility of the new technique. The protocol was performed using the system schematically shown in FIG. 4. The first subject 26 was a healthy male, age 28 years, body weight 172 lbs, vital capacity 5000 ml, and experienced at performing breathing maneuvers. The second subject 26 was a healthy male, age 23 years, body weight 175 lbs, and vital capacity 5200 ml who was not experienced at performing breathing maneuvers. The anatomical deadspace was thus estimated to be 200 ml and 198 ml for the two subjects, respectively.

The subjects 26 performed a series of single oral exhalation breathing maneuvers against a small resistance (>5 cmH$_2$O) for the isolation of the nasal cavity. The subjects 26 first performed vital capacity maneuvers at a constant exhalation flow of ~50 ml/s and ~250 ml/s as described by the ATS and ERS guidelines to determine the plateau concentration of NO. A constant flow was facilitated by a Starling resistor 28 (Hans Rudolph, Kansas City, Mo.) in which the resistance could be altered to achieve the desired flow rate. The subjects 26 then performed a series of single exhalations following a period of breathholding. The period of breathholding was either 10, 20, 30, or 45 seconds, and each maneuver was repeated five times. It is this maneuver which represents the invention, and the steps are as follows:

1) A nose-clip is placed on the subjects nose to prevent any nasal flow of of air, and the subjects is asked to inspire NO-free air from the reservoir 30 to total lung capacity (until they cannot inhale any additional air.
2) The expiratory valve 43 is then turned such that the subject cannot expire any air. Thus, the patient is holding their breath. During the breathhold, the subject 26 exerts an expiratory effort against a closed valve 43 to maintain a positive pressure of >5 cm H$_2$O in the expiratory line 44, and the NO sampling line 34 sampls air from the zero NO reservoir 30.
3) At the end of the desired breathhold time, or just prior to exhalation, the valve 32 on the NO sampling line 34 is changed to sample from the exhaled breath and the exhalation valve 43_____is opened allowing the patient 26 to expire.
4) During the exhalation phase, the subject is asked to maintain a constant expiratory effort maintaining the pressure in the expiratory line 44>5 cm H$_2$O. The expiratory flow rate progressively decreases during the exhalation from an initial value of ~300 ml/s (~6% of the vital capacity per second) to ~50 ml/s (~1% of the vital capacity per second). To facilitate such a flow rate pattern, the expiratory resistance is altered throughout the maneuver, while the subject 26 was instructed not to change the expiratory effort. By monitoring online the flow signal and progressively increasing the resistance, we can produce the desired flow rate pattern.
5) The subject expires until no more air can be expelled. This constitutes the end of the breathing maneuver.

An exponentially decreasing flow rate with volume which ranges from ~6% of the vital capacity per second to ~1% of the vital capacity per second was set as a target, although this is not required. This choice satisfies two basic requirements for the flow rate pattern: 1) a uniform residence time distribution of the exhaled gas in the airways 10, and 2) minimal acceleration of a single bolus of gas inside the airways 10.

In order to achieve an even distribution for the residence times sampled during an exhalation flow maneuver, one needs the residence time, $T_{res}(t)$, for any differential bolus of air to be linear function of time. Thus, it is easily demonstrated that if the exhalation flow rate decreases exponentially with exhaled volume, one can achieve this linear dependence between $T_{res}(t)$ and t.

By specifying an exponentially decreasing $\dot{V}_E$ with V, and by using the relationship $\dot{V}_E = dV/dt$, one can establish the following relationship:

$$\dot{V}_E = \dot{V}_{E0} e^{-cV} = 1/(\dot{V}_{E0}^{-1} + ct) \tag{A1}$$

where $\dot{V}_{E0}$ is the initial flowrate and c is a linear multiplier. Then, any differential bolus entering at time t will reside in the airways time $T_{res}(t)$ such that the following relationship holds (similar to Eq. 5):

$$V_{air} = \int_{t}^{t+\tau_{res}(t)} \dot{V}_E \, dt \tag{A2}$$

One can then insert Eq. A1 into Eq. A2 and derive the following linear relationship between $T_{res}(t)$ and t:

$$T_{res}(t) = (e^{cV_{air}} - 1)((c\dot{V}_{E0})^{-1} + t) \tag{A3}$$

In addition, it follows from Eq. A1 that the ratio of exiting and entering velocities is the same for every differential bolus of gas:

$$\frac{\dot{V}_E(t + \tau_{res})}{\dot{V}_E(t)} = e^{-cV_{air}} \tag{A4}$$

Thus, the particular flow rate profile described by Eq. A1 provides the same relative change between the entering and exiting flow rates of any exhaled gas bolus. For our experiments, where flow rate change is from ~300 to ~50 ml/s over a period of 15–20 sec and 3 to 4 lt of exhaled volume, the approximate values of $\dot{V}_{E0}$ and c are ~300 ml/s and ~0.50 $l^{-1}$, respectively. Thus, from Eq. A4, the exiting velocity is ~90% of the entering velocity thus providing support for the key assumption made in our governing equation as described in the Methods and in the Discussion.

NO concentration was measured using a chemiluminescence NO analyzer 22 (NOA280, Sievers, Inc., Boulder, Colo.). An operating reaction cell pressure was maintained at 7.5 mm Hg, which provided a sampling flow rate of 250 ml/min (FIG. 4). The analyzer 22 was calibrated on a daily basis using a certified NO gas (25 ppm in N2, INO max Sensormedics, CA). The zero point calibration was performed with an NO filter 36 (Sievers, Inc., Boulder, Colo.). Due to a small drift in the calibration of the analyzer 22 during the day, we performed zero point calibration immediately prior to the collection of a profile. The flow rate was measured using a pneumotachometer 24 (RSS100, Hans Rudolph Inc., Kansas City, Mo.). The pneumotachometer 24 was calibrated daily and was set to provide the flow in units of ml/s STPD (Standard Pressure Temperature Dry). Pressure was measured by a pressure meter 42 model RSS100 manufactured by Hans Rudolph Inc.(Kansas City, Mo.). The analog signals of flow and NO were digitized using an A/D card 38 at a rate of 50 Hz and stored on a personal computer 40 for further analysis. While computer 40 is arranged and configured by conventional programming to perform the functions disclosed in this specification, it is to be expressly understood that computer 40 may be substituted by equivalent means, such as logic circuits, digital signal processors and other analog and/or digital signal processing circuitry.

Parameter Estimation.

Identification of the unknown parameters ($C_{alv,ss}$, $D_{NO,air}$, $J_{NO,max}$) is accomplished by nonlinear least square minimization. Assuming a constant variance error in the measurement renders ordinary least squares sufficient for parameter estimation. Minimization of the sum of square of the residuals, $R_{LS}$, between the model's prediction and the experimental data was accomplished utilizing a conjugated direction minimization algorithm.

Figure 5A:
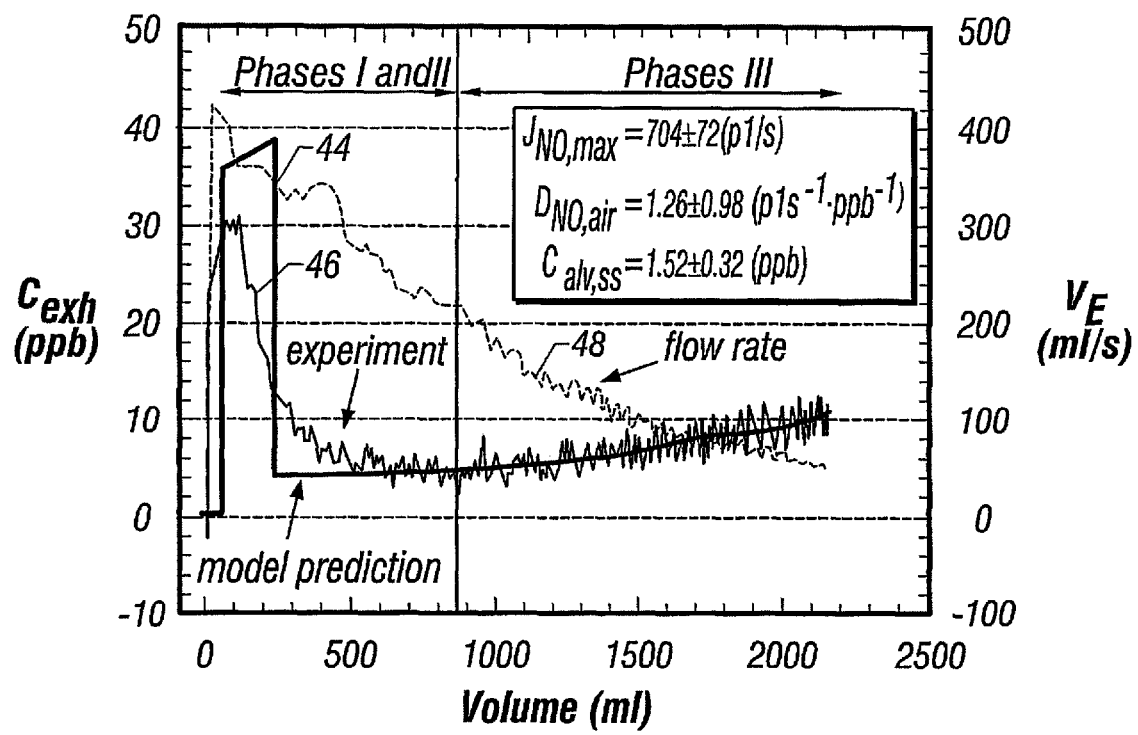
FIGS. 5A and 5B are graphs which show the exhaled NO concentration profile following a 20-second breathhold shown as a function of exhaled volume in FIG. 5A or time in FIG. 5B. The light colored line is exhaled NO concentration (ppb) and the dashed line is the exhalation flow rate (A) or pressure (B). The dark line represents the best-fit model prediction of the exhalation curve using non-linear least squares regression. The optimal values for three unknown input parameters, $C_{alv,ss}$, $D_{NO,air}$, and $J_{NO,max}$ are shown for this particular maneuver.
Figure 5B:
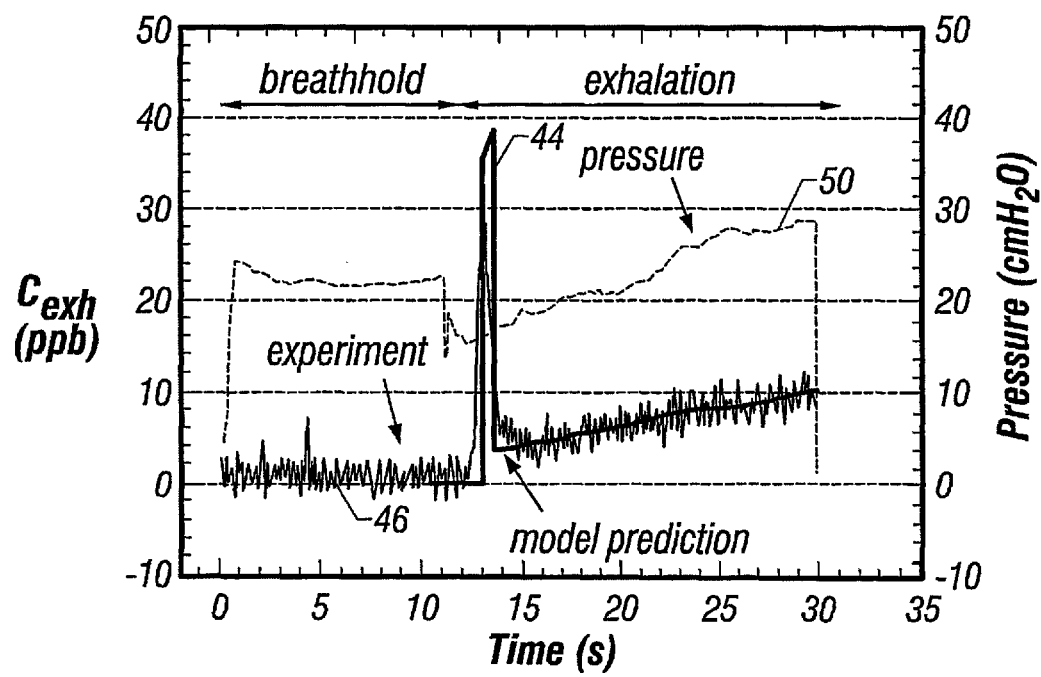

FIGS. 5A and 5B present a representative exhalation profile from the first subject 26 simulated by the model. FIGS. 5A and 5B are graphs which show the exhaled NO concentration profile following a 20-second breathhold shown as a function of exhaled volume in FIG. 5A or time in FIG. 5B. The light colored line 46 is exhaled NO concentration (ppb) and the dashed line 48 is the exhalation flow rate in FIG. 5A or pressure 50 in FIG. 5B. The dark line 44 represents the best-fit model prediction of the exhalation curve using non-linear least squares regression. The optimal values for three unknown input parameters, $C_{alv,ss}$, $D_{NO,air}$, and $J_{NO,max}$ are shown for this particular maneuver. The model prediction is shown in the heavy continuous line 44 while the actual experimental data is shown in the light line 46. The model does not precisely predict Phase I and II of the exhalation profile, where the accumulated NO during breathholding in the conducting airways and transition region 10 of the lungs exits the mouth. This discrepancy is attributed to axial diffusion that our model neglects. Although the precise shape of Phase I cannot be accurately simulated with the model, the absolute amount of NO in Phase I and II can be predicted. Thus, our technique utilizes the information from Phase I and II (where $T_{res}$ is large and hence the sensitivity to $D_{NO,air}$ is high) by forcing the model to simulate the total amount of NO exiting in Phase I and II of the exhalation in addition to simulating the precise $C_{exh}$ over Phase III. Thus, the fitting of the experimental data will include minimization of the sum of two terms: 1) the squared residual in the average concentrations in Phase I and II weighted by the number of data points, and 2) the sum of the squared residual of $C_{exh}$ in Phase III of the exhalation profile according to the following relationship:

$$R_{LS} = n_{I,II} \cdot \left( \left( \sum_{i=1}^{n_{I,II}} C^*_{exh,i} \cdot \Delta V_{I,II} \right) / V_{I,II} - \left( \sum_{i=1}^{n_{I,II}} C_{exh,i} \cdot \Delta V_{I,II} \right) / V_{I,II} \right)^2 + \sum_{i=1}^{n_{III}} (C^*_{exh,i} - C_{exh,i})^2 \tag{7}$$

where $n_{I,II}$ and $V_{I,II}$ are the number of data points and volume in Phase I and II, $n_{III}$ and $V_{III}$ are the number of data points and volume in Phase III, $C^*_{exh}$ is the model-predicted concentration, and $\Delta V_{I,II}$ is the change in volume between consecutive data points ($\dot{V}_E * dt$). To ensure complete emptying of the airway compartment 10 following breathhold, we define the transition from Phase II to Phase III as the point in the exhalation for which the slope ($dC_{exh}/dV$) of the exhalation profile is zero.

Identifiability and Uncertainty Analysis.

A high sensitivity is a necessary but not a sufficient condition for an accurate estimation of the parameters. Dependence between the parameters may render them unidentifiable even when their sensitivities are significant.

Thus, although the sensitivity analysis suggests experimental conditions for improving the estimation of the parameters, a better index is needed to describe the accuracy of our estimation.

Once the matrix $\underline{X}$ of the sensitivity coefficients at every $t_i$ can be estimated (i.e. $\underline{X}_{i,j}=S_i^{sr}(t_j)$), a confidence region for the estimated parameters can be acquired from the variance-covariance matrix of the estimation.

Assuming additive zero mean and normally distributed measurement errors, and errorless measured inputs, the $100(1-\alpha)\%$ confidence region for the ordinary least square estimation of the vector of inputs, $\underline{Y}_{LS}$, is approximated from:

$$(\underline{Y}_{LS}-\beta)^T P^{-1}(\underline{Y}_{LS}-\beta)=pF_{1-\alpha}(p, n-p) \quad (8)$$

where $\beta$ is their expected true value, and $F_{1-\alpha}$ is the F-statistic test for the number of estimated parameters, p, (i.e. 3 in our case), and the number of data points, n. For an ordinary least square estimation with the additional assumption of constant variance, and uncorrelated errors, the covariance matrix $\underline{P}$ is, $$\underline{P}=(\underline{X}^T\underline{X})^{-1}\sigma^2 \quad (9)$$

and an unbiased estimation of $\sigma^2$ is given by, $$s^2=E(\sigma^2)=R_{LS}/(n-p) \quad (10)$$

The approximate confidence regions are the interior of the hyperellipsoids provided by Eq. 9. The maximum range of the parameters in these contours can be estimated from the eigenvalues of P as follows:

$$\Delta \bar{I}_{1-\alpha,i}{}^m=(\pm pF_{1-\alpha}(p,n-p)e_1(\lambda_1)^{-1/2})_{i-row}/Y_i \quad (11)$$

where $\lambda_1$ is the smaller eigenvalue of the P matrix and $e_1$ the corresponding eigenvector. Thus $\Delta \bar{I}_{1-\alpha;i}{}^m$ provides the normalized (by the estimated value of parameter i) confidence region of the estimated parameters for a single maneuver, or an intra-maneuver confidence interval.

We can also define a normalized intra-subject (inter-maneuver) confidence interval by using the standard deviation, SD, of the estimate of each of the parameters for the five repeated maneuvers:

$$\Delta \bar{I}^s_{1-\alpha,i} = \pm \frac{SD}{\sqrt{n_m}} t_{1-\alpha}/Y_i \quad (12)$$

where $n_m$ is the number of breathing maneuvers, and $t_{1-\alpha}$ is the critical t-value for $n_m-1$ degrees of freedom.

Figures 1, 6A:
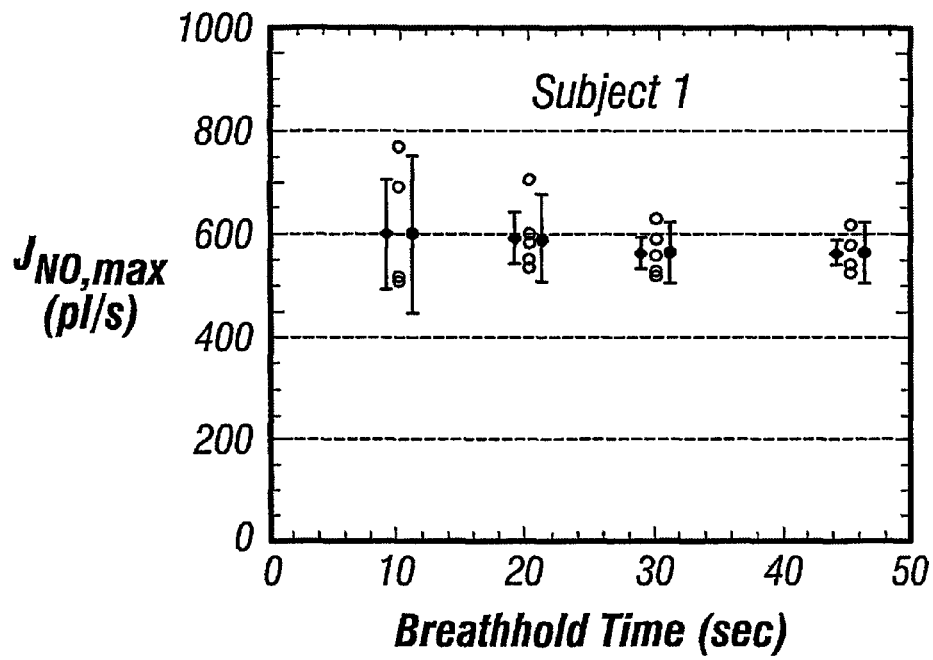
FIGS. 6A–6C are graphs illustrating the optimal parameter values for $J_{NO,max}$ (A), $D_{NO,air}$ (B), and $C_{alv,ss}$ (C) following five repeated decreasing flow rate exhalation breathing maneuvers (open circles) following four different breathhold times (10, 20, 30, and 45 seconds) for two subjects.
Figures 2, 6A:
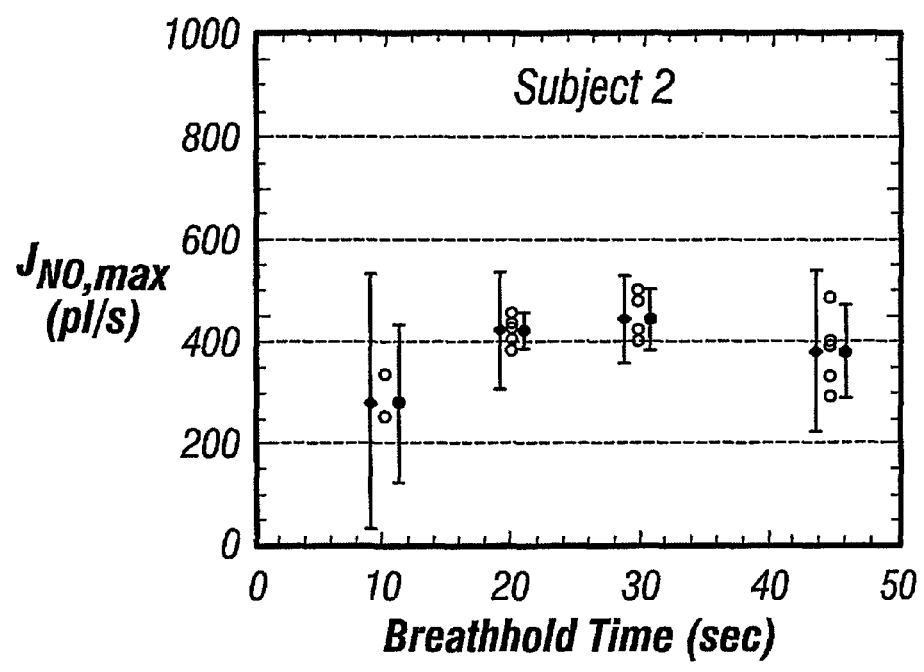
Figures 1, 6B:
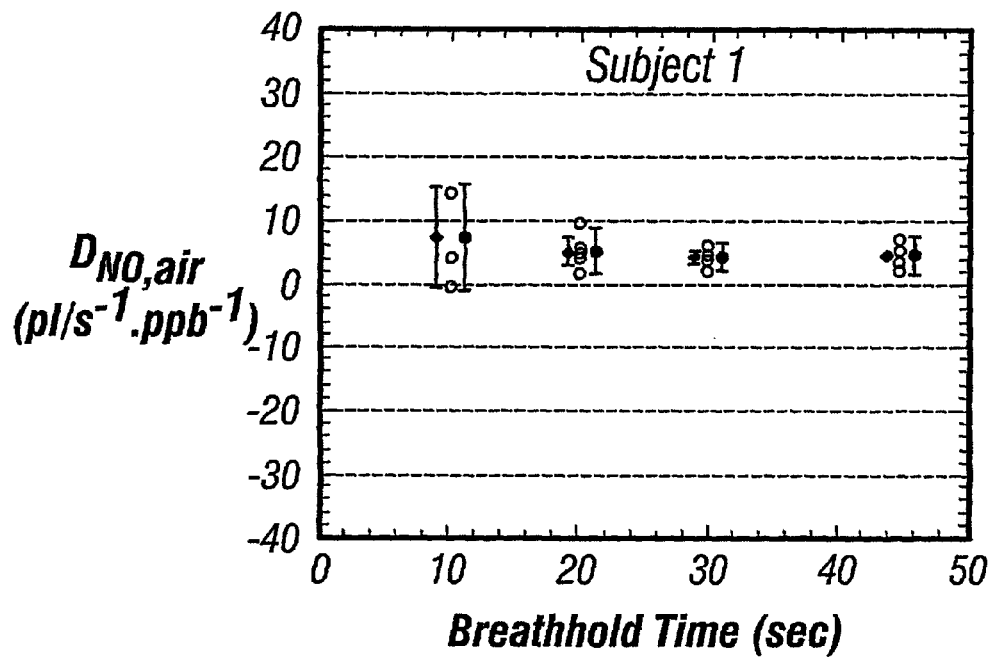
Figures 2, 6B:
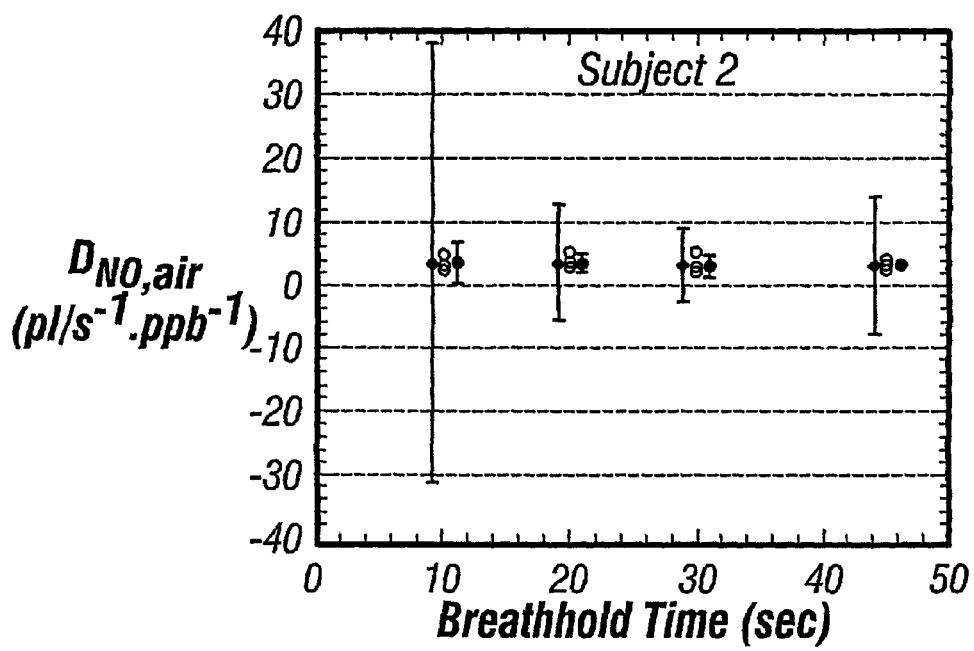
Figures 1, 6C:
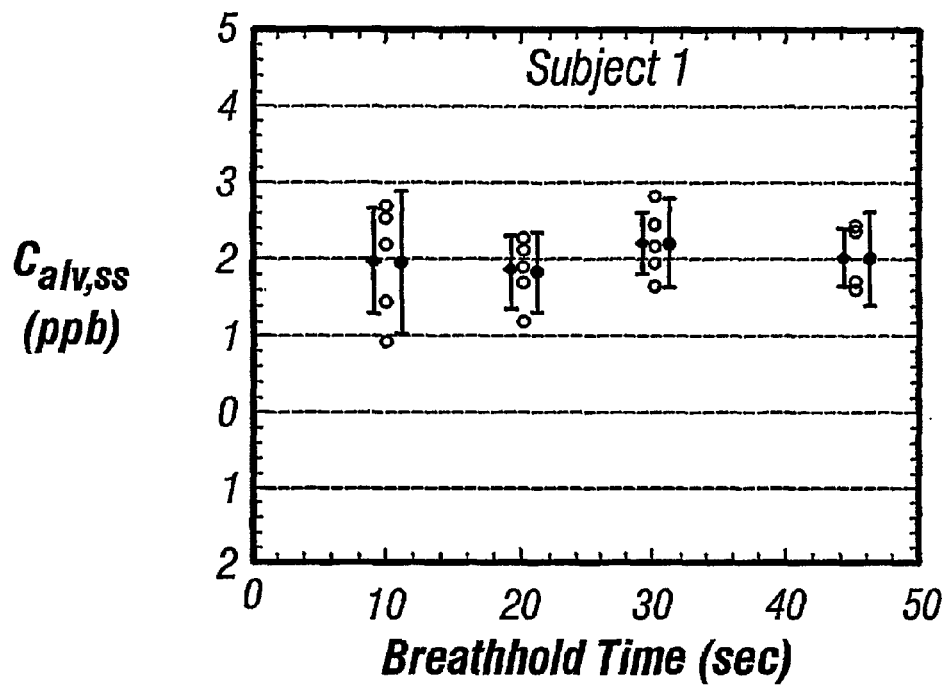
Figures 2, 6C:
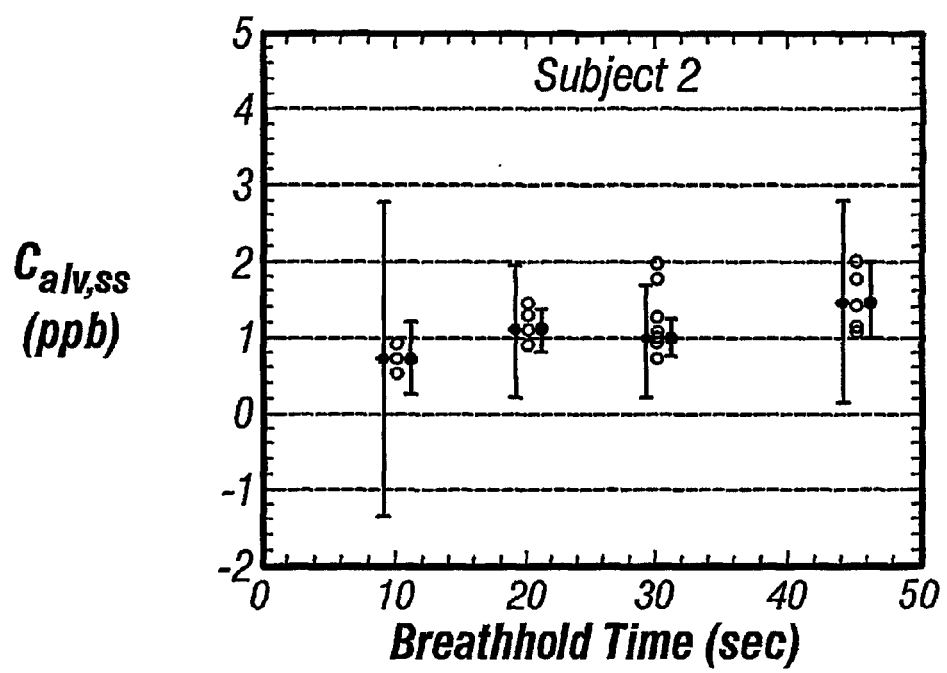

FIGS. 6A, B, and C presents the estimated parameters ($J_{NO,max}$, $D_{NO,air}$, and $C_{alv,ss}$, respectively) for each of the five repeated breathing maneuvers (four maneuvers for a 45 second breathhold) for both subjects 26 (subject #1 left-hand panels and subject #2 right-hand panels). FIGS. 6A–6C are graphs illustrating the optimal parameter values for $J_{NO,max}$ (A), $D_{NO,air}$ (B), and $C_{alv,ss}$ (C) following five repeated decreasing flow rate exhalation breathing maneuvers (open circles) following four different breathhold times (10, 20, 30, and 45 seconds) for two subjects. Subject #1 (left-hand panels) is experienced at performing breathing maneuvers, and Subject #2 (right-hand panels) was naive. The solid diamonds represent the mean optimal parameter value and the error bars are the mean intra-maneuver 95% confidence intervals. The solid squares represent the mean optimal parameter value and the error bars are the mean intra-subject 95% confidence intervals. To the left of the five repeated estimates for each parameter is the mean estimated value with error bars representing the mean $\Delta \bar{I}_{0.95,i}{}^m$ (Eq. 11). That is, for each maneuver an independent estimate of the confidence region is estimated from Eq. 11, and the error bar represents the mean of these intra-maneuver confidence region estimates. To the right of the five repeated estimates is the mean estimated value with error bars representing the mean $\Delta \bar{I}_{0.95,i}{}^s$ (Eq. 12, or intra-subject variability). The mean values for $J_{NO,max}$, $D_{NO,air}$, and $C_{alv,ss}$ do not depend on breathold time, and range from 580–600 pl/s, 4.6–7.1 pl·s$^{-1}$ ppb$^{-1}$, and 1.8–2.2 ppb for Subject #1, and 280–440 pl/s, 3.7–4.1 pl·s$^{-1}$·ppb$^{-1}$, and 0.73–1.5 ppb for Subject #2.

The intra-maneuver estimate of $J_{NO,max}$ steadily improves (as evidenced by a decreasing confidence interval) as the breathhold time increases from 10 to 30 seconds. The mean $\Delta \bar{I}_{0.95;i}{}^s$ is 17% and 89% for Subject #1 and #2 at a 10 second breathhold and decreases to 6.5% and 19% for a 30 second breathhold, respectively. No significant improvement is seen with a 45 second breathhold. The same trend is observed for $D_{NO,air}$ except the magnitude of the uncertainty is larger. The mean $\Delta \bar{I}_{0.95;i}{}^s$ is 89% and 941% for for Subject #1 and #2 at a 10 second breathhold and decreases to 19% and 159% for a 30 second breathhold, respectively.

A similar, although more modest trend with breathhold time is observed for $C_{alv,ss}$. The mean $\Delta \bar{I}_{0.95,C_{alv,ss}}{}^s$ improves by increasing the breathhold time from 10 to 20 seconds (34% and 280% to 26% and 78% for Subject #1 and #2, respectively), but then remains nearly constant for breathhold times >20 seconds. Importantly, there is no statistical difference between the estimated values for any of the parameters at different breathhold times, only a change in the estimated confidence interval.

The intra-subject estimate of the three parameters consistently improves (as evidenced by a decreasingconfidence interval) as the breathhold time increases from 10 to 20 seconds with modest or no significant improvement for breathhold times >20 seconds. The mean $\Delta \bar{I}_{0.95,J_{NO,max}}{}^m$, is 25% and 41% for Subject #1 and #2 at a 10 second breathhold which decreases to 13% and 8.3% for a 20 second breathhold. The mean $\Delta \bar{I}_{0.95,D_{NO,air}}{}^m$ is 114% and 90% for Subject #1 and #2, respectively, for a 10 second breathhold and decreases to 45% and 32% for a 20 second breathhold, respectively. For $C_{alv,ss}$, the mean $\Delta \bar{I}_{0.95,C_{alv,ss}}{}^m$ is 47% and 63% for Subject #1 and #2, respectively, for a 10 second breathhold and decreases to 28% and 24% for a 20 second breathhold, respectively.

In general, the mean value for $\Delta \bar{I}_{0.95;i}{}^s$ differs from the mean value of $\Delta \bar{I}_{0.95,i}{}^m$ due to the fact that $\Delta \bar{I}_{0.95,i}{}^s$ depends inversely on the square root of the number of maneuvers performed (Eq. 12) and on the reproducibility of the experimental conditions and measurements. In addition, it is also of interest to note that the intra-maneuver confidence intervals for Subject #1 are much smaller than for Subject #2, yet the intra-subject confidence intervals are, in general, larger.

Figure 7:
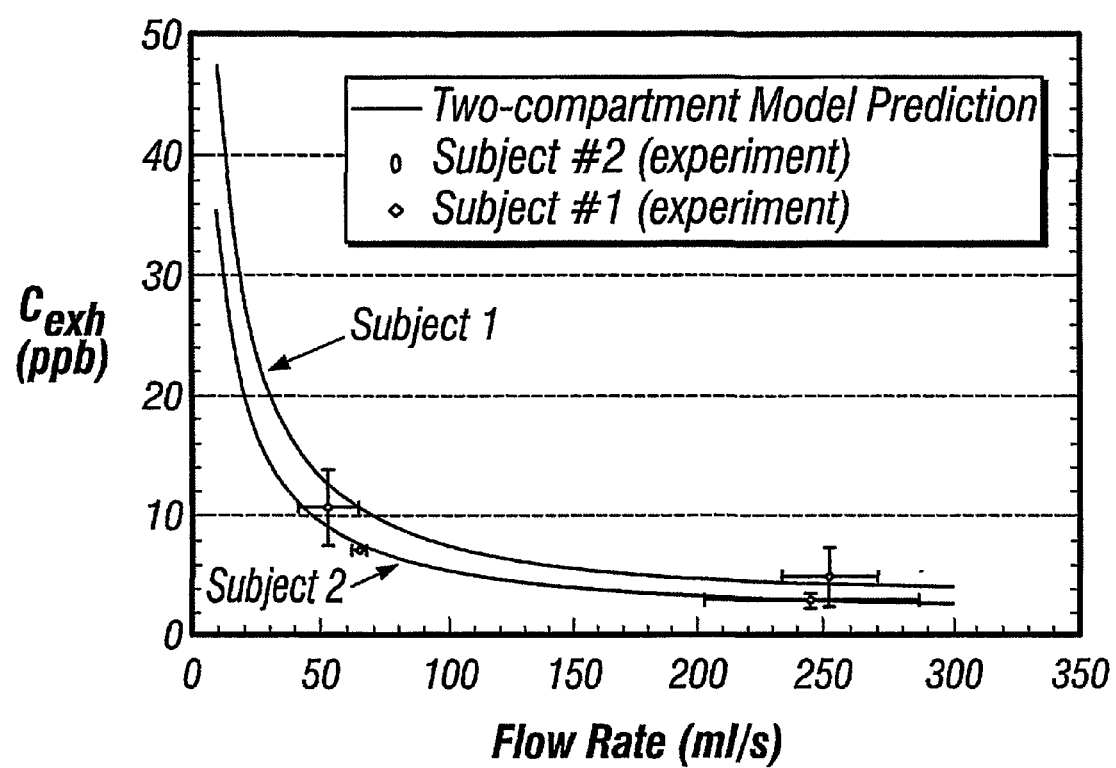
FIG. 7 is a graph of the exhaled concentration at end-exhalation, $C_{exh,ee}$, shown as a function of the constant exhalation flow rate for both subjects.

In FIG. 7, NO plateau concentration, $C_{exh,ee}$ (concentration at end-exhalation),from a constant exhalation flow rate is plotted as a function of $\dot{\nu}_E$. FIG. 7 is a graph of the exhaled concentration at end-exhalation, $C_{exh,ee}$, shown as a function of the constant exhalation flow rate for both subjects. Error bars in the experimental data points represent 95% confidence intervals. Two exhalation flow rates are shown (~50 and ~250 ml/s) based on ATS and ERS recommendations. The solid lines are the model prediction of the $C_{exh,ee}$ at a constant exhalation flow rate using the mean value of the optimal parameter values determined from the flow rate maneuvers following by 20-second breathhold. The model prediction (solid line) is calculated using the mean estimated parameters from the five repeated 20 second breathhold maneuvers. Mean $C_{exh,ee}$ (±95% confidence interval) from the experimental maneuvers with the recommended constant flow rates are also presented. The predicted NO plateau concentrations are in close agreement with the experimental measurements. Importantly, FIG. 7 demonstrates that once the unknown flow-independent parameters have been estimated, the model can be utilized to accurately predict the NO plateau concentration, at least for constant flow rates between 50–300 ml/s.

Figure 8A:
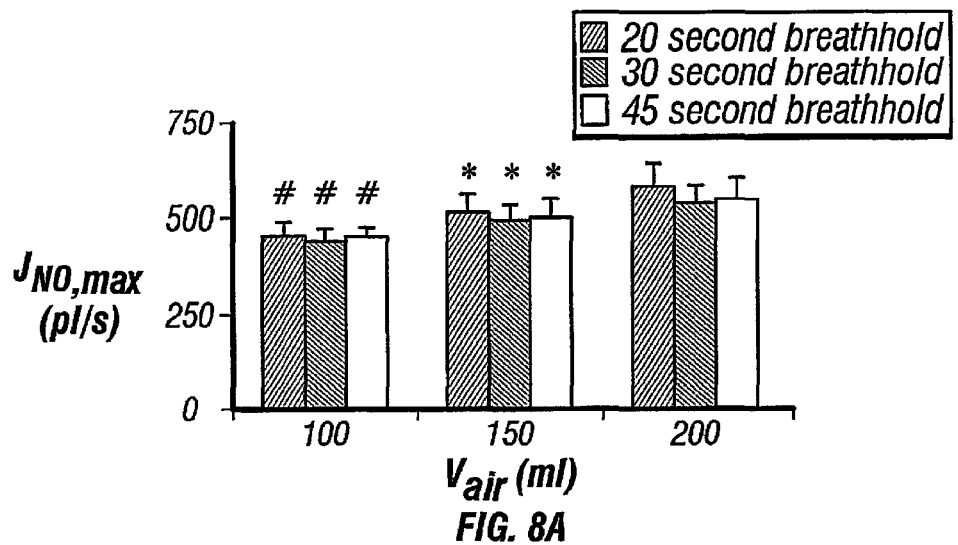
FIGS. 8A–8C are bar charts where the three estimated parameters, $J_{NO,max}$ (A), $D_{NO,air}$ (B), and $C_{alv,ss}$ (C), are shown as a function of the choice for $V_{air}$ for each of three breathhold times (20, 30, and 45 seconds).
Figure 8B:
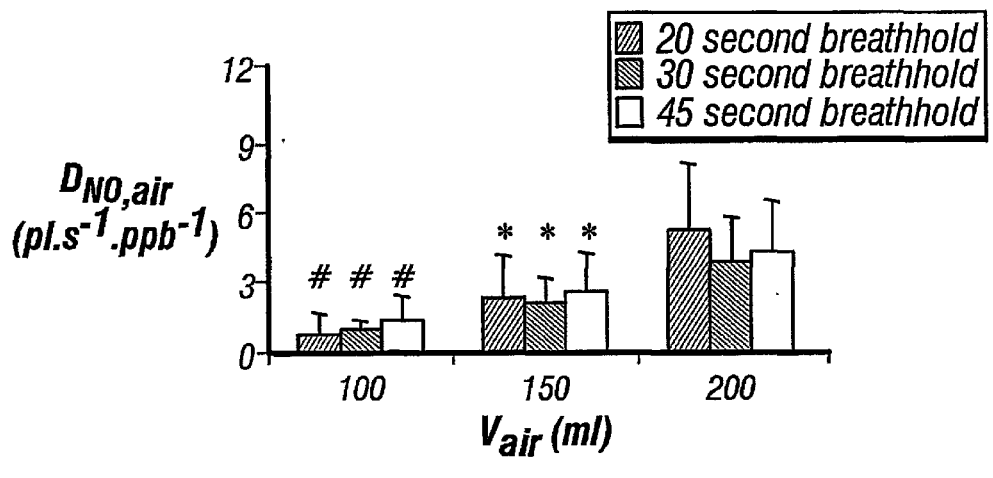
Figure 8C:
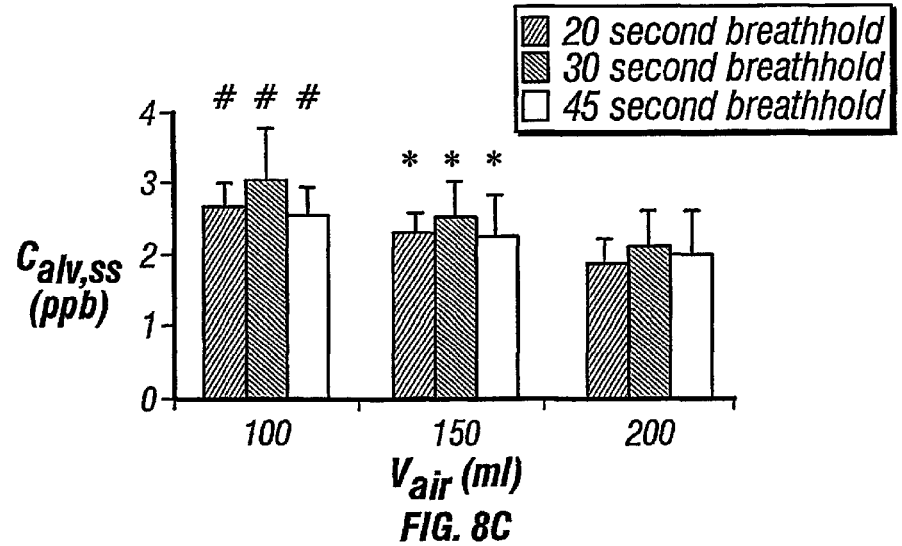

In FIGS. 8A–8C, the effect of $V_{air}$ in the estimation of the unknown parameters of interest is investigated. FIGS. 8A–8C are bar charts where the three estimated parameters, $J_{NO,max}$ (A), $D_{NO,air}$ (B), and $C_{alv,ss}$ (C), are shown as a function of the choice for $V_{air}$ for each of three breathhold times (20, 30, and 45 seconds). 200 ml is the estimated value of the anatomical deadspace for the subject based on the subjects ideal body weight in pounds plus the age in years. *statistically different from $V_{air}$=200 ml. #statistically different from $V_{air}$=150 ml. Statistical significance was determined using a paired Student t-test and P<0.05. The 20, 30, and 45 second breathhold maneuvers were reanalyzed for Subject #1 with two smaller values for $V_{air}$ (100 and 150 ml) instead of the control value of 200 ml. There is a statistically significant difference in the estimation of all three parameters (p<0.01) with decreasing $V_{air}$ at each breathhold time. There is a positive correlation between the estimated values of $J_{NO,max}$ and $D_{NO,air}$ with $V_{air}$ and a negative correlation for $C_{alv,ss}$. The percent change in the estimated parameters per ml change in $V_{air}$ has averaged values of 0.2%, 1.5%, and −0.3% for $J_{NO,max}$, $D_{NO,air}$, and $C_{alv,ss}$, respectively.

In summary, what has thus been presented is a method for the analysis and interpretation of exhaled NO data. This technique can estimate three flow independent parameters ($J_{NO,max}$, $D_{NO,air}$, and $C_{alv,ss}$) from a single exhalation maneuver, which can comprehensively characterize the exhalation NO profile. The technique requires only a single breathing maneuver, and is therefore less cumbersome to perform than other techniques, which require multiple breathing maneuvers. Thus, the technique has the potential to be applied to many different diseases and gather information on parameters that will likely provide more specific and sensitive information about NO metabolism, and thus inflammation.

The backward integration of the flow signal (Eq. 4 and 5) provides powerful flexibility as a specific flow rate profile is not required. One requires knowledge of only the specific exhalation flow rate profile such that the backward integration is possible. Thus, the method is very general and can be applied essentially to any given single exhalation profile, or even tidal breathing in which the flow varies naturally in time during each breath. However, we utilized an exhalation maneuver with the following characteristics such that our model assumptions and simplifications were still valid, yet we were still able to accurately determine the unknown parameters: 1) the exhalation flow rate pattern produces exhaled boluses of gas with a wide range of uniformly distributed residence times to distinguish alveolar and airway contributions to exhaled NO (i.e., uniquely determine the three unknown parameters), 2) the rate of change in exhalation flow rate is small enough that each bolus of air resides approximately the same amount of time in the different parts of the airways (i.e. minimal acceleration requirement), and 3) easy to perform.

In agreement with the prior art models we assumed in this study that the linear dependence of $J'_{NO}$ on $C_{air}$ is constant along the airway tree. In fact, at any given axial position, the flux of NO will depend on many variables in addition to $C_{air}$ such as tissue thickness, endogenous production and consumption rates, and airway diameter; thus, the dependence of $J'_{NO}$ on $C_{air}$ does not necessarily remain the same with axial position. It has been recently demonstrated that $D_{NO,air}$ for asthmatics was increased relative to healthy subjects even after treatment with corticosteroids. In an earlier study, it was also reported that, in healthy lungs, a significant fraction of exhaled NO arises from the trachea (~45%) suggesting that the larger airways and mouth (~7%) were the primary source of oral exhaled NO. This does not exclude the lower airways from contributing NO. In fact, the lower airways, together with the alveolar region, must account for the remaining ~48%. Our model (as well as previous models) assumes that the contribution of NO from airways is evenly distributed per unit airway volume. The volume of the trachea (~35–40 ml) accounts for ~20–25% of the physiological deadspace ($V_{air}$). Thus, the larger airways are likely contributing a greater share per unit airway volume in healthy lungs, and the distribution of NO flux ($J_{NO,max}$ and $D_{NO,air}$) may change in disease states. This feature of NO exchange does not invalidate our governing equation, but does place a requirement that the exhalation flow rate not change rapidly during the exhalation maneuver.

Rapid changes in the flow will result in significant acceleration (or deceleration) of a differential bolus of gas while traversing the airways. As a result, the bolus of gas will reside different amounts of time in the different parts of the airways thus rendering our governing equation invalid. As shown above the maximum change in the flow rate during exhalation such that the residence time of any differential gas bolus not change by >10%. Since we cannot preclude a non-uniform NO exchange distribution, such a flow profile minimizes the potential error in the estimation of $D_{NO,air}$ and $J_{NO,max}$.

Our sensitivity analysis (FIG. 3) demonstrates that a range of flow rates (or residence times) is necessary to uniquely determine the three parameters. This can be understood if one considers the limiting cases. At very high flow rates, the residence time in the airway compartment 10 approaches zero, and thus very little NO is absorbed by the exhalate. Thus, the exhaled NO concentration approaches that of $C_{alv,ss}$. The sensitivity is therefore highest for $C_{alv,ss}$ at very small airway compartment residence times; however, very little information can be extracted about the airway compartment 10. Conversely, as the residence time increases, a progressively increasing proportion of the exhaled NO is derived from the airway compartment 10; thus, the parameters which characterize the airway compartment 10 ($J_{NO,max}$ and $D_{NO,air}$) can be uniquely determined.

To estimate $D_{NO,air}$, much longer residence times are necessary. This is observed in FIG. 3 and can be explained by Eq. 3. $D_{NO,air}$ only becomes significant (or impacts $J'_{NO}$) when $C_{air}$ is large enough such that the second term in Eq. 3 becomes significant. Thus, the exhalation flow rate must be low such that NO can accumulate in the airways. This increases $C_{air}$ and decreases the driving force for diffusion of NO in the airstream. One choice in handling this problem is to increase the flow rate range by including smaller flows (higher residence times). The prior art has utilized flows less than 10 ml/s to accomplish estimation of $D_{NO,air}$. Alternatively, we utilized a pre-expiratory breathhold (limit of zero exhalation flow rate) to achieve long residence times. We believe this alternative provides equivalent information about the airway compartment 10, and is more easily performed by the subject 26, as well as more easily recorded by the investigator.

An exhalation that spans a wide range of flows may not however be sufficient unless each flow is sustained for a sufficient time to allow a bolus of air to traverse the airways at a specific flow rate. For example a 10 ml/s flow rate in a 150 ml airway will result in an exhaled bolus of gas with a residence time of 15 seconds. Thus, to characterize the concentration of such a bolus, the flow rate should be sustained for at least 15 seconds In a single exhalation maneuver with a dynamically changing flow rate, lower flows should be sustained for more time than high flows in order to collect exhaled concentrations that accurately span a wide range of residence times. Ideally, the residence time should also be distributed uniformly over this wide range such as to acquire the same amount of data at any given residence time.

Based on the above specifications, we propose a single exhalation maneuver that includes a pre-expiratory breathhold time, followed by a flow rate pattern that decreases approximately exponentially with volume from approximately 6% of the VC per second (300 ml/s in our subjects) to approximately 1% of the VC per second (50 ml/s in our subjects). Such a pattern provides exhaled boluses of gas whose flow rates do not change significantly during their passage through the airways (difference of entering to exiting velocity less than 10%. At the same time, the residence times of the exiting boluses are approximately uniformly distributed over a range between 0.5 and 3 seconds (see shaded area in FIG. 3). This provides the necessary sensitivity for the estimation of $C_{alv,ss}$ and $J_{NO,max}$.

The dependence of our parameter estimation on the choice of $V_{air}$ presents a potential problem (FIG. 8). The dependence of the parameters, particularly $D_{NO,air}$, on $V_{air}$ is due to the fact that the model's prediction for the NO concentration in the airways during breathholding depends on the choice of $V_{air}$. For example, if $V_{air}$ decrease from 200 to 100 ml, the concentration in the airway compartment 10 will increase more rapidly; thus, to predict the experimental concentration, $J_{NO,max}$ and $D_{NO,air}$ would need to decrease (FIG. 8).

However, the parameter most impacted by the choice of $V_{air}$ is $D_{NO,air}$ which is determined primarily from the shape of the exhalation profile in Phase I and II (or the breathhold). During a breathhold, the NO emitted into the airway compartment 10 will disperse in either direction due to molecular diffusion and cardiac mixing. Based on a molecular diffusion coefficient of 0.27 cm²/s for NO in the gas phase, a conservative length for dispersion during the breathhold is 2–4 cm. This axial distance is approximately equal to that between generations 6–15 based on Weibel's symmetric lung model. Thus, axial dispersion will tend to create a shape for Phase I and II similar to that generated if the NO flux was uniformly distributed, thus mitigating the impact of a non-uniform distribution in NO flux. Hence, even if the distribution of NO flux is altered in disease, the choice for $V_{air}$ should not have a significant impact on the relative change in the parameter estimates due to disease.

Covariance analysis (Eq. 8) provides an a priori estimate (i.e. without the need of multiple maneuvers) for the accuracy of our predictions. Thus, it can be utilized as a criterion for rejecting a profile or for specifying sufficient experimental conditions for parameter estimation (flow rate range, breathhold time). The covariance analysis suggests that a breathhold time of 20 seconds in combination with the specific flow rate pattern are adequate for the specific subject in determining the parameters of interest. This theoretical prediction was validated by repeated measurements. Although a longer breathhold time may provide increased accuracy of the estimate of $D_{NO,air}$, the gain is minimal and the effort on the part of the patient increases dramatically. A 20 second breathhold may not be possible for those subjects with more advanced lung disease who are hypoxic or hypercarbic, and an alternative technique may be necessary. For example, further characterization of this technique in a given lung disease population may determine that $J_{NO,max}$ is as good an indicator of disease status as $D_{NO,air}$, and thus the breathhold may not be necessary in all patient populations. Additional studies on more normal subjects and those with inflammatory diseases are necessary before a formal recommendation can be made.

Although there was not a significant variation in the mean values of the parameters between Subject #1 and #2, there were differences in the confidence intervals. For Subject #2, the intra-maneuver confidence intervals were significantly larger than Subject #1. The intra-maneuver confidence interval is a positive function of $R_{LS}$. Thus, a large $\Delta \bar{I}_{0.95,i}^m$ reflects a large $R_{LS}$ and, provided the instrument error did not change between subject testing, can be considered an index of the accuracy or appropriateness of the two-compartment model. Thus, there may be significant variation amongst the normal population in how well the two-compartment model can simulate NO exchange dynamics. In contrast, intra-subject confidence intervals for Subject #2 were very similar, or slightly improved, compared to Subject #1. $\Delta \bar{I}_{0.95,i}^s$ is a positive function of the deviation of the estimate from the population mean (Eq. 12); thus, it provides an index of the maneuver-to-maneuver reproducibility. Thus, our naive subject (Subject #2) was able to reproduce the breathing maneuvers to a similar degree as our experienced subject (Subject #1). This finding suggests that the maneuver is relatively simple to perform, and that patients from many sub-populations may be able to perform the maneuver with minimal training.

Recently, ATS provided recommendations for standardized procedures for the measurement of exhaled NO. They recommended a constant exhalation flow rate maneuver of 50 ml/s and recording of the NO plateau value. The flow rate should be maintained within 10% of this value throughout the exhalation. The recommendations acknowledged that theoretical predictions from our earlier work and others suggest that derivation of additional parameters of potential physiological importance, by analyzing the dependence of $C_{exh}$ on $\dot{V}_E$, may be achievable.

The significance and utility of the parameters estimated in this study for identification and/or monitoring of inflammatory diseases need to be examined through extensive application of these methods. At this point such experimental data are limited. Prior art researchers have applied their method in asthmatics with some intriguing results. They found that $D_{NO,air}$ is 4-fold higher in asthmatics and that this increase is independent of steroid treatment. In contrast, the NO plateau concentration does not change dramatically between normals and asthmatics treated with steroids. Perhaps the most promising utility of this technique is to follow patients longitudinally, and correlate intra-subject changes in these parameters with important clinical decisions such as therapeutic dose. Thus, if the same $V_{air}$ is used for a given subject over time (i.e., $V_{air}$ (ml)=subjects ideal body weight in pounds+age in years), one should be able to accurately determine changes in NO exchange parameters over time. Finally, there are other techniques such as the single exhalation $CO_2$ profile that might be used in conjunction with this technique as an independent assessment of physiological deadspace.

An alternative method of describing the linear dependence of $J'_{NO}$ on the bulk gas phase concentration is to utilize a mass transfer coefficient (or transfer factor) and a concentration difference:

$$J'_{NO} = \left(\frac{D_{NO,air}}{V_{air}}\right)(\overline{C}_{tiss,air} - C_{air}) \quad (12)$$

where $\overline{C}_{tiss,air}$ is the mean (over radial position) concentration within the tissue phase, and $D_{NO,air}$ is equivalent to a mass transfer coefficient or transfer factor. Mathematically, this representation of NO flux is equivalent to Eq. 3 where $J_{NO,max}=D_{NO,air}*\overline{C}_{tiss,air}$. Thus, the airway compartment 10 is now alternatively characterized by $D_{NO,air}$ and $\overline{C}_{tiss,air}$. We can estimate $\overline{C}_{tiss,air}$ by taking the ratio of $J_{NO,max}$ to $D_{NO,air}$. For Subject #1, the mean values of $\overline{C}_{tiss,air}$ (with inter-maneuver 95% confidence intervals) are 89 ppb (68%), 155 ppb (92%), 152 ppb (63%), and 144 ppb (64%) for 10, 20, 30, and 45 second breathhold, respectively. One estimate from the 10 second breathing maneuver was discarded as it produced a large negative value that greatly skewed the estimate. For Subject #2, the mean values of $\overline{C}_{tiss,air}$ (with inter-maneuver 95% confidence intervals) are 85 ppb (124%), 112 ppb (26%), 133 ppb (28%), and 95 ppb (28%) for 10, 20, 30, and 45 second breathhold, respectively. The variance of $\overline{C}_{tiss,air}$ is similar to the other three parameters, and the mean value does not depend strongly on breathhold time. Although the mean values for the two subjects are similar to that recently predicted by others, the variance of this data cannot be compared as they report only a inter-subject variability for a technique that utilizes multiple breathing maneuvers.

The invention thus describes a new technique to characterize flow-independent parameters ($J_{NO,max}$, $D_{NO,air}$, and $C_{alv,ss}$), which can characterize NO exchange dynamics in the lungs. The maneuver entails appropriate analysis of only a single exhalation breathing maneuver that should be tolerated by a wide range of subjects. In addition, our results suggest that the stringent requirements on the flow rate that ATS and ERS recommends are not needed. With proper analysis of a variable flow rate maneuver, one can estimate flow-independent parameters that potentially provide more specificity and sensitivity to disease status. If necessary, one can then use the model to predict the NO plateau concentration at a constant flow (FIG. 7). This could be of importance, especially for young and diseased subjects that have difficulty sustaining a constant expiratory flow.

Thus the invention contemplates accommodating inter-subject variability in a variety of key populations including healthy adults and children, as well as inflammatory diseases such as bronchial asthma, chronic obstructive pulmonary disease, and cystic fibrosis. For example, while a conscious breathing maneuver including a breathhold has been described, it is expressly within the scope of the invention that it could be applied to tidal breathing, namely the natural breathing rhythm of the subject at rest. In the case of infants, very small children, severely diseased individuals, and unconscious subjects tidal breathing may be the only practical respiratory behavior, which is available to be monitored. Because of the low flows and variability of flow rates characteristic of tidal breathing, prior art methodologies have not been able to analyze such populations, which are now susceptible to analysis according to the invention.

Many alterations and modifications may be made by those having ordinary skill in the art without departing from the spirit and scope of the invention. Therefore, it must be understood that the illustrated embodiment has been set forth only for the purposes of example and that it should not be taken as limiting the invention as defined by the following claims. For example, notwithstanding the fact that the elements of a claim are set forth below in a certain combination, it must be expressly understood that the invention includes other combinations of fewer, more or different elements, which are disclosed in above even when not initially claimed in such combinations.

The words used in this specification to describe the invention and its various embodiments are to be understood not only in the sense of their commonly defined meanings, but to include by special definition in this specification structure, material or acts beyond the scope of the commonly defined meanings. Thus if an element can be understood in the context of this specification as including more than one meaning, then its use in a claim must be understood as being generic to all possible meanings supported by the specification and by the word itself.

The definitions of the words or elements of the following claims are, therefore, defined in this specification to include not only the combination of elements which are literally set forth, but all equivalent structure, material or acts for performing substantially the same function in substantially the same way to obtain substantially the same result. In this sense it is therefore contemplated that an equivalent substitution of two or more elements may be made for any one of the elements in the claims below or that a single element may be substituted for two or more elements in a claim. Although elements may be described above as acting in certain combinations and even initially claimed as such, it is to be expressly understood that one or more elements from a claimed combination can in some cases be excised from the combination and that the claimed combination may be directed to a subcombination or variation of a subcombination.

Insubstantial changes from the claimed subject matter as viewed by a person with ordinary skill in the art, now known or later devised, are expressly contemplated as being equivalently within the scope of the claims. Therefore, obvious substitutions now or later known to one with ordinary skill in the art are defined to be within the scope of the defined elements.

The claims are thus to be understood to include what is specifically illustrated and described above, what is conceptionally equivalent, what can be obviously substituted and also what essentially incorporates the essential idea of the invention.

I claim:

1. A method for determining flow independent parameters characteristic of nitrogen monoxide exchange and of lung function in a subject during one or more exhalations during which flow rate of exhalation varies in time comprising:

exhaling into a mouthpiece in which the resistance to airflow can vary in time and;

measuring exhaled nitrogen monoxide concentration, $C_{exh}$, from said subject as a function of time; and simultaneously measuring volumetric exhalation flow rate, $\dot{V}_E$, as a function of time with measurement of exhaled nitrogen monoxide concentration;

backwards integrating said volumetric exhalation flow rate, $\dot{V}_E$, over time to convert exhalation time to residence time of each exhaled bolus of gas in said airway compartment of said subject; and selecting said flow independent parameters to fit said measured nitrogen monoxide concentration as a function of time given residence time obtained by backwards integration.

2. The method of claim 1 further comprising:

estimating $V_{air}$, which is the volume of said airway compartment of said subject, and;

measuring $V_{ds}$ which is the dead space volume or volume expired prior to observing an NO signal, and where backwards integrating said exhalation flow rate, $\dot{V}_E$, over time to convert exhalation time to residence time of each exhaled bolus of gas in an airway compartment in said subject is performed in a computer according to a Case I or Case II integration where:

Case I(Phase I and II of exhalation): $\int_{t-\tau_{res}(t)}^{t+t_{ds}} \dot{V}_E(t')dt' = 0$ Case II(Phase III of exhalation): $\int_{t-\tau_{res}(t)}^{t+t_{ds}} \dot{V}_E(t')dt' = V_{air} + V_{ds}$ where t is time, $t_{ds}$ is convective transport delay time in the dead space volume, $T_{res}$: is residence time of each differential gas bolus in said airway compartment.

3. The method of claim 2 where selecting said flow independent parameters to fit said measured nitrogen monoxide concentration as a function of time given residence time obtained by backwards integration comprises estimating three flow independent parameters $C_{alv,ss}$, $D_{NO,air}$, $J_{NO,max}$ from $C_{exh}$ as a function of $T_{res}(t)$, where $C_{alv,ss}$ is the steady state alveolar concentration of nitrogen monoxide, $D_{NO,air}$ is the diffusing capacity of nitrogen monoxide in said airway compartment, $J_{NO,max}$ is the maximum total molar flux of nitrogen monoxide from the airway wall, $C_{exh}$ is the exhaled concentration of nitrogen monoxide, and $T_{res}(t)$ is the residence time of each differential gas bolus in said airway compartment as a function of time, t.

4. The method of claim 3 where estimating said three flow-independent parameters $C_{alv,ss}$, $D_{NO,air}$, $J_{NO,max}$ from $C_{exh}$ as a function of $T_{res}(t)$, comprising performing said estimation by relating said three flow-independent parameters $C_{alv,ss}$, $D_{NO,air}$, $J_{NO,max}$ and $C_{exh}$ to measured exhaled concentration in a computer in the relationship given by:

$$C_{exh}(t+t_{ds}) = \left(C_{in}(t-\tau_{res}) - \frac{J_{NO,\max}}{D_{NO,air}}\right)e^{-\frac{D_{NO,air}}{V_{air}}\tau_{res}(t)} + \frac{J_{NO,\max}}{D_{NO,air}}$$

where $C_{in}$ is the inlet concentration of nitrogen monoxide to said airway compartment.

5. The method of claim 1 where selecting said flow independent parameters to fit said measured nitrogen monoxide concentration as a function of time given residence time obtained by backwards integration comprises estimating three flow independent parameters $C_{alv,ss}$, $D_{NO,air}$, $J_{NO,max}$ from $C_{exh}$ as a function of $T_{res}(t)$, where $C_{alv,ss}$ is the steady state alveolar concentration of nitrogen monoxide, $D_{NO,air}$ is the diffusing capacity of nitrogen monoxide in said airway compartment, $J_{NO,max}$ is the maximum total molar flux of nitrogen monoxide from the airway wall, $C_{exh}$ is the exhaled concentration of nitrogen monoxide, and $T_{res}(t)$ is the residence time of each differential gas bolus in said airway compartment as a function of time, t.

6. The method of claim 5 where estimating said three flow-independent parameters $C_{alv,ss}$, $D_{NO,air}$, $J_{NO,max}$ from $C_{exh}$ as a function of $T_{res}(t)$, comprises performing said estimation by relating said three flow-independent parameters $C_{alv,ss}$, $D_{NO,air}$, $J_{NO,max}$ and $C_{exh}$ to measured exhaled concentration in a computer in the relationship given by:

$$C_{exh}(t+t_{ds}) = \left(C_{in}(t-\tau_{res}) - \frac{J_{NO,\max}}{D_{NO,air}}\right)e^{-\frac{D_{NO,air}}{V_{air}}\tau_{res}(t)} + \frac{J_{NO,\max}}{D_{NO,air}}$$

where $C_{in}$ is the inlet concentration of nitrogen monoxide to said airway compartment.

7. The method of claim 1 where measuring nitrogen monoxide concentration as a function of time comprises performing said measurement of said exhaled bolus of gas with a distribution of residence times ranging from approximately 0.5 seconds to a minimum of approximately 10 seconds for an adult sized lung after a breathold.

8. The method of claim 1 where measuring nitrogen monoxide concentration as a function of time and simultaneously measuring volumetric exhalation flow rate, $\dot{V}_E$, as a function of time comprises performing said measurements with a distribution of residence times ranging from approximately 0.5 seconds to approximately a minimum of 10 seconds for an adult sized lung after a breathhold.

9. The method of claim 1 where measuring nitrogen monoxide concentration as a function of time and simultaneously measuring volumetric exhalation flow rate, $\dot{V}_E$, as a function of time comprises performing said measurements with a residence time of said exhaled bolus of gas of at least ten seconds by performing a preexpiratory breathhold.

10. The method of claim 9 where performing said preexpiratory breathhold comprises performing a breathhold of duration between 10–45 seconds.

11. The method of claim 1 where exhaling into said mouthpiece with variable resistance to airflow comprises providing an approximately exponentially decreasing flow of exhalation in time.

12. The method of claim 1 where exhaling into said nitrogen monoxide concentration analyzer comprises providing an uniform distribution of residence time and a minimal acceleration of said exhaled bolus of gas in said airway compartment.

13. The method of claim 1 where exhaling into said nitrogen monoxide concentration analyzer comprises establishing said residence time for each differential bolus of gas as an approximate linear function of time, t.

14. The method of claim 13 where establishing said residence time for each differential bolus of gas as a linear function of time, t, comprises exhaling such that $$\dot{V}_E = 1/(\dot{V}_{E0}^{-1} + ct)$$

is approximated, where $\dot{V}_E$ is the time dependent rate of exhalation, $\dot{V}_{E0}$ is the initial flow rate of exhalation and c is a linear multiplier.

15. The method of claim 1 where selecting said flow independent parameters to fit said measured nitrogen monoxide concentration as a function of time given residence time obtained by backwards integration comprises optimizing said flow independent parameters by performing a nonlinear least square minimization of $C_{exh}$.

16. The method of claim 15 where optimizing said flow independent parameters by performing a nonlinear least square minimization of $C_{exh}$ comprises minimizing a sum of two terms: 1) the squared residual in the average concentrations in Phase I and II weighted by the number of data points, and 2) the sum of the squared residual of $C_{exh}$ in Phase III of the exhalation profile according to the following relationship:

$$R_{LS} = n_{I,II} \cdot \left( \left( \sum_{i=1}^{n_{I,II}} C^*_{exh,i} \cdot \Delta V_{I,II} \right) / V_{I,II} - \left( \sum_{i=1}^{n_{I,II}} C_{exh,i} \cdot \Delta V_{I,II} \right) / V_{I,II} \right)^2 + \sum_{i=1}^{n_{III}} (C^*_{exh,i} - C_{exh,i})^2 \quad (7)$$

where $n_{I,II}$ and $V_{I,II}$ are the number of data points and volume in Phase I and II respectively, $n_{III}$ and $V_{III}$ are the number of data points and volume in Phase III, $C^*_{exh}$ is the model-predicted concentration, and $\Delta V_{I,II}$ is the change in volume between consecutive data points, ($\dot{V}_E$*dt), in Phase I and II respectively.

17. The method of claim 1 where exhaling into a mouthpiece in which in which flow rate and nitrogen monoxide concentration are simultaneously measured includes tidal breathing by said subject.

18. An apparatus for determining flow independent parameters of lung function in a subject during one exhalation during which flow rate of exhalation varies in time comprising:

a sampling line into which said subject exhales;

a nitrogen monoxide analyzer coupled to said sampling line to measure exhaled nitrogen monoxide concentration, $C_{exh}$, from said subject as a function of time;

a flow meter coupled to said sampling line to measure to measure volumetric exhalation flow rate, $\dot{V}_E$, as a function of time; and a computer coupled to said nitrogen monoxide analyzer and to said flow meter to backwards integrate said volumetric exhalation flow rate, $\dot{V}_E$, over time to convert exhalation time to residence time of each exhaled bolus of gas in said airway compartment of said subject; and to select said flow independent parameters to fit said measured nitrogen monoxide concentration as a function of time given residence time obtained by backwards integration.

19. The apparatus of claim 18 where said flowmeter measures $V_{ds}$ which is the dead space volume or volume expired prior to observing a NO signal, and where said computer is arranged and configured to backwards integrate said exhalation flow rate, $\dot{V}_E$, over time to convert exhalation time to residence time of each exhaled bolus of gas in an airway compartment in said subject is performed in a computer according to a Case I or Case II integration where:

Case I (Phase I and II of exhalation): $\int_{t-\tau_{res(t)}}^{t+t_{ds}} \dot{V}_E(t')dt' = 0$ Case II (Phase III of exhalation): $\int_{t-\tau_{res(t)}}^{t+t_{ds}} \dot{V}_E(t')dt' = V_{air} + V_{ds}$ where t is time, $t_{ds}$ is convective transport delay time in the dead space volume, $T_{res}$: is residence time of each differential gas bolus in said airway compartment.

20. The apparatus of claim 18 where said computer is arranged and configured to estimate three flow-independent parameters $C_{alv,ss}$, $D_{NO,air}$, $J_{NO,max}$ from experimentally determined $C_{exh}$ as a function of $T_{res}(t)$, where $C_{alv,ss}$ is the steady state alveolar concentration of nitrogen monoxide, $D_{NO,air}$ is the diffusing capacity of nitrogen monoxide in said airway compartment, $J_{NO,max}$ is the maximum total molar flux of nitrogen monoxide from the airway wall, $C_{exh}$ is the exhaled concentration of nitrogen monoxide, and $T_{res}(t)$ is the residence time of each differential gas bolus in said airway compartment as a function of time, t.

21. The apparatus of claim 20 where said computer is arranged and configured to estimate three flow-independent parameters $C_{alv,ss}$, $D_{NO,air}$, $J_{NO,max}$ from experimentally measured $C_{exh}$ as a function of $T_{res}(t)$, where $C_{alv,ss}$ is the steady state alveolar concentration of nitrogen monoxide, $D_{NO,air}$ is the diffusing capacity of nitrogen monoxide in said airway compartment, $J_{NO,max}$ is the maximum total molar flux of nitrogen monoxide from the airway wall, $C_{exh}$ is the exhaled concentration of nitrogen monoxide, and $T_{res}(t)$ is the residence time of each differential gas bolus in said airway compartment as a function of time, t.

22. The apparatus of claim 21 where said computer performs said estimation by relating said three flow-independent parameters $C_{alv,ss}$, $D_{NO,air}$, $J_{NO,max}$ and experimentally measured $C_{exh}$ in a computer in the relationship given by:

$$C_{exh}(t+t_{ds}) = \left(C_{in}(t-\tau_{res}) - \frac{J_{NO,max}}{D_{NO,air}}\right)e^{-\frac{D_{NO,air}}{V_{air}}\tau_{res}(t)} + \frac{J_{NO,max}}{D_{NO,air}}$$

where $C_{in}$ is the inlet concentration of nitrogen monoxide to said airway compartment.

23. The apparatus of claim 22 where said computer performs said estimation by relating said three flow-independent parameters $C_{alv,ss}$, $D_{NO,air}$, $J_{NO,max}$ and experimentally measured $C_{exh}$ in a computer in the relationship given by:

$$C_{exh}(t+t_{ds}) = \left(C_{in}(t-\tau_{res}) - \frac{J_{NO,max}}{D_{NO,air}}\right)e^{-\frac{D_{NO,air}}{V_{air}}\tau_{res}(t)} + \frac{J_{NO,max}}{D_{NO,air}}$$

where $C_{in}$ is the inlet concentration of nitrogen monoxide to said airway compartment.

24. The apparatus of claim 18 where said nitrogen monoxide analyzer performs said measurements on said exhaled bolus of gas with a distribution of residence times ranging from approximately 0.5 to a minimum of approximately 10 seconds for an adult sized after a breathhold.

25. The apparatus of claim 18 where said nitrogen monoxide analyzer performs said measurements on said exhaled bolus of gas with a residence time of at least one second after a pre-expiratory breathhold.

26. The apparatus of claim 18 where said nitrogen monoxide analyzer performs said measurements on said exhaled bolus of gas with a residence time of at least ten seconds after a pre-expiratory breathhold.

27. The apparatus of claim 26 where said nitrogen monoxide analyzer performs said measurements on said exhaled bolus of gas with a distribution of residence times between approximately 0.5 and 3 seconds for an adult sized lung after expulsion of air in the airway during a pre-expiratory breathhold of 10, 20, 30 or 45 seconds.

28. The apparatus of claim 18 where said nitrogen monoxide analyzer is provided with an approximately exponentially decreasing flow of exhalation.

29. The apparatus of claim 18 where said nitrogen monoxide analyzer is provided with an approximate uniform distribution of residence time and a minimal acceleration of said exhaled bolus of gas in said airway compartment.

30. The apparatus of claim 18 where said nitrogen monoxide analyzer is provided with differential boluses of gas with a residence time which is an approximate linear function of time, t.

31. The apparatus of claim 30 where said nitrogen monoxide analyzer is provided with differential boluses of gas with a residence time such that $$\dot{V}_E = 1/(\dot{V}_{E0}^{-1} + ct)$$

is approximated, where $\dot{V}_E$ is the time dependent rate of exhalation, $\dot{V}_{E0}$ is the initial flow rate of exhalation and c is a linear multiplier.

32. The apparatus of claim 18 where said computer is arranged and configured to optimize said flow independent parameters by performing nonlinear least square minimization of $C_{exh}$.

33. The apparatus of claim 32 where said computer is arranged and configured to optimize said flow independent parameters by performing a nonlinear least square minimization of $C_{exh}$ comprises minimizing a sum of two terms: 1) the squared residual in the average concentrations in Phase I and II weighted by the number of data points, and 2) the sum of the squared residual of $C_{exh}$ in Phase III of the exhalation profile according to the following relationship:

$$R_{LS} = n_{I,II} \cdot \left(\left(\sum_{i=1}^{n_{I,II}} C^*_{exh,i} \cdot \Delta V_{I,II}\right)\bigg/ V_{I,II} - \left(\sum_{i=1}^{n_{I,II}} C_{exh,i} \cdot \Delta V_{I,II}\right)\bigg/ V_{I,II}\right)^2 + \sum_{i=1}^{n_{I,II}} (C^*_{exh,i} - C_{exh,i})^2 \quad (7)$$

where $n_{I,II}$ and $V_{I,II}$ are the number of data points and volume in Phase I and II respectively, $n_{III}$ and $V_{III}$ are the number of data points and volume in Phase III, $C^*_{exh}$ is the model-predicted concentration, and $\Delta V_{I,II}$ is the change in volume between consecutive data points, ($\dot{V}_E * dt$), in Phase I and II respectively.

34. The apparatus of claim 18 where said nitrogen monoxide concentration analyzer samples tidal breathing by said subject.

* * * * *

UNITED STATES PATENT AND TRADEMARK OFFICE
CERTIFICATE OF CORRECTION

PATENT NO. : 6,866,637 B2
DATED : March 15, 2005
INVENTOR(S) : Steven C. George and Nikolaos Tsoukias It is certified that error appears in the above-identified patent and that said Letters Patent is hereby corrected as shown below:

Column 1,
Line 7, insert:
-- This invention was made with the Government support under Grant No. HL60636 awarded by the National Institutes of Health and Government support under Grant No. 9619340 awarded by the National Science Foundation. The Government has certain rights in this invention --.

Signed and Sealed this

Fourteenth Day of March, 2006

JON W. DUDAS
*Director of the United States Patent and Trademark Office*